(12) United States Patent
Reimels et al.

(10) Patent No.: US 12,303,399 B2
(45) Date of Patent: *May 20, 2025

(54) EXPANDABLE LORDOTIC INTERBODIES AND RELATED METHODS

(71) Applicant: Alphatec Spine, Inc., Carlsbad, CA (US)

(72) Inventors: William Reimels, Hamilton, OH (US); Max C. Zemezonak, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 18/317,796

(22) Filed: May 15, 2023

(65) Prior Publication Data
US 2023/0285163 A1 Sep. 14, 2023

Related U.S. Application Data

(63) Continuation of application No. 17/190,768, filed on Mar. 3, 2021, now Pat. No. 11,690,732.

(60) Provisional application No. 62/985,610, filed on Mar. 5, 2020, provisional application No. 63/062,663, filed on Aug. 7, 2020.

(51) Int. Cl.
*A61F 2/44* (2006.01)
*A61F 2/30* (2006.01)
*A61F 2/46* (2006.01)

(52) U.S. Cl.
CPC ............ *A61F 2/447* (2013.01); *A61F 2/4611* (2013.01); *A61F 2002/30156* (2013.01); *A61F 2002/30224* (2013.01); *A61F 2002/30433* (2013.01); *A61F 2002/30471* (2013.01); *A61F 2002/3054* (2013.01); *A61F 2002/30556* (2013.01); *A61F 2002/30579* (2013.01);
(Continued)

(58) Field of Classification Search
CPC ...... A61F 2/44–447; A61F 2002/30156; A61F 2002/30224; A61F 2002/30433; A61F 2002/30471; A61F 2002/3054; A61F 2002/30556; A61F 2002/30579; A61F 2002/30784; A61F 2002/30971; A61F 2002/4627

See application file for complete search history.

(56) References Cited

U.S. PATENT DOCUMENTS 8,105,382 B2  1/2012  Olmos
8,382,842 B2  2/2013  Greenhalph
(Continued)

OTHER PUBLICATIONS

International Bureau, "Notification Concerning International Preliminary Report on Patentability," for International Application No. PCT/US2021/030972, issued Sep. 6, 2022, mailed Sep. 15, 2022.
(Continued)

*Primary Examiner* — Nicholas J Plionis
(74) *Attorney, Agent, or Firm* — Robert Winn

(57) ABSTRACT

The present disclosure relates to an expandable interbody that includes superior and inferior shells enclosing a control mechanism that includes interlocking proximal and distal cages as well as an adjustment screw that longitudinally translates the distal cage relative to the proximal cage and thereby expands interbody by pushing apart the distal ends of the superior and inferior shells.

20 Claims, 9 Drawing Sheets

(52) U.S. Cl.
CPC .............. *A61F 2002/30784* (2013.01); *A61F 2002/30971* (2013.01); *A61F 2002/4627* (2013.01)

(56) References Cited

U.S. PATENT DOCUMENTS

| | | |
|---|---|---|
| 8,568,481 B2 | 10/2013 | Olmos |
| 8,632,595 B2 | 1/2014 | Weiman |
| 8,679,183 B2 | 3/2014 | Glerum |
| 8,685,098 B2 | 4/2014 | Glerum |
| 8,845,731 B2 | 9/2014 | Weiman |
| 9,034,041 B2 | 5/2015 | Wolters |
| 9,320,610 B2 | 4/2016 | Alheidt |
| 9,370,434 B2 | 6/2016 | Weiman |
| 9,492,288 B2 | 11/2016 | Wagner |
| 9,566,168 B2 | 2/2017 | Glerum |
| 9,585,766 B2 | 3/2017 | Robinson |
| 9,585,767 B2 | 3/2017 | Robinson |
| 9,788,971 B1 | 10/2017 | Stein |
| 9,801,733 B2 | 10/2017 | Wolters |
| 9,907,673 B2 | 3/2018 | Weiman |
| 9,962,270 B2 | 5/2018 | Alheidt |
| 10,034,765 B2 | 7/2018 | Blain |
| 10,034,769 B2 | 7/2018 | Baynham |
| 10,098,759 B2 | 10/2018 | Weiman |
| 10,111,758 B2 | 10/2018 | Robinson |
| 10,137,009 B2 | 11/2018 | Weiman |
| 10,278,830 B1 | 5/2019 | Walker |
| 10,383,741 B2 | 8/2019 | Butler |
| 10,426,632 B2 | 10/2019 | Butler |
| 10,561,502 B2 | 2/2020 | Bernard et al. |
| 10,639,166 B2 | 5/2020 | Weiman |
| 10,646,351 B2 | 5/2020 | Blain |
| 10,687,963 B2 | 6/2020 | Jimenez et al. |
| 10,709,575 B2 | 7/2020 | Robinson |
| 10,779,957 B2 | 9/2020 | Weiman |
| 10,898,344 B2 | 1/2021 | Alheidt |
| 10,925,752 B2 | 2/2021 | Weiman |
| 11,013,617 B2 | 5/2021 | Weiman |
| 11,690,732 B2 * | 7/2023 | Reimels ................ A61F 2/4455 623/17.11 |
| 2008/0140207 A1 | 6/2008 | Olmos et al. |
| 2008/0177275 A1 | 7/2008 | Wing et al. |
| 2014/0236297 A1 | 8/2014 | Iott et al. |
| 2015/0272743 A1 | 10/2015 | Jimenez et al. |
| 2016/0120660 A1 | 5/2016 | Melkent et al. |
| 2016/0166396 A1 * | 6/2016 | McClintock ............ A61F 2/446 623/17.16 |
| 2016/0331542 A1 | 11/2016 | Faulhaber et al. |
| 2016/0338845 A1 | 11/2016 | Ashleigh |
| 2017/0105844 A1 | 4/2017 | Kuyler et al. |
| 2017/0112630 A1 * | 4/2017 | Kuyler ................ A61F 2/4455 |
| 2018/0125671 A1 | 5/2018 | Bernard |
| 2018/0289505 A1 | 10/2018 | Foley et al. |
| 2018/0296361 A1 | 10/2018 | Butler |
| 2019/0021868 A1 | 1/2019 | Ludwig et al. |
| 2019/0060083 A1 | 2/2019 | Weiman |
| 2019/0201209 A1 | 7/2019 | Branch et al. |
| 2022/0160515 A1 | 5/2022 | Bougere et al. |

OTHER PUBLICATIONS

USPTO acting as International Searching Authority, "International Search Report and Written Opinion," for International Application No. PCT/US2021/043419, mailed Nov. 1, 2021.

* cited by examiner

EXPANDABLE LORDOTIC INTERBODIES AND RELATED METHODS

RELATED APPLICATIONS

This application is a continuation of U.S. application Ser. No. 17/190,768, filed Mar. 3, 2021, which claims priority to U.S. Provisional Application Nos. 62/985,610, filed Mar. 5, 2020, and 63/062,663, filed Aug. 7, 2020, the entire contents of both of which are herein incorporated by reference.

BACKGROUND

The present disclosure relates to expandable implants such as spinal interbody and intervertebral body devices and, more particularly, to vertebral interbodies that are expandable after placement in the spine.

Fusion cages, as well as other types of interbodies and devices, are frequently utilized in spinal surgery inside a vertebra or in the disc space between respective vertebra (interbody). With interbody devices, one or more such spinal bodies are placed between vertebrae to provide support and promote fusion between adjacent vertebrae. Such fusion may be necessary because of disease, injury, general deterioration, or a congenital problem.

The goal of most spinal surgeries is to minimize the trauma of the surgery itself. One way to minimize the trauma is to create as small an access port as possible to reach the surgical site; however, a small access port then limits the size of the tools and implants that can pass through the access port.

A few interbody devices, however, are now being made that are expandable. Expandable interbodies are initially smaller than traditional non-expandable (static) interbodies such that the expandable interbodies may be more easily inserted and/or implanted into the disc space. The expandable interbodies, once positioned in the disc space, are expanded to a desirable size to achieve the amount of expansion necessary for the particular patient.

SUMMARY

The present disclosure relates to an expandable lordotic interbody that can be inserted into a disc space in a collapsed state so as to minimize trauma to the patient and then expanded to achieve a desired lordosis. The interbody includes superior and inferior shells enclosing a control mechanism. The shells can each include at least one graft window with the respective windows being, in some embodiments, aligned with each other. The control mechanism includes interlocking proximal and distal cages as well as an adjustment screw that longitudinally translates the distal cage relative to the proximal cage. Translation of the distal cage expands the interbody by pushing apart the respective distal ends of the superior and inferior shells.

According to some embodiments, one or both of the superior shell and the inferior shell includes in a side wall of the shell an angled slot extending distally and toward a central plane that bisects the interbody into superior and inferior halves. The interlocking proximal and distal cages contained within the superior and inferior shells are configured to translate longitudinally relative to each other by way of an adjustment screw that is threadingly engaged with either the proximal or the distal cage.

In some embodiments, the adjustment screw is threadingly engaged with a distally located threaded bore in the distal cage, while a proximal end of the adjustment screw is secured to the proximal cage so as to be fixed longitudinally relative to the proximal cage. This can be achieved in some cases with a pin that is inserted into a distal end of the proximal cage, the pin being configured to engage with a radial groove or flange on the adjustment screw.

In some embodiments, the adjustment screw is threadingly engaged with a distally located threaded bore in the proximal cage, while a distal end of the adjustment screw is configured to abut and, in some embodiments, apply pressure to an inside surface of a distal end of the distal cage. At least a portion of the distal end of the adjustment screw may be tapered or rounded so as to reduce the friction between it and the distal cage. In some embodiments, one or more rods are set in or secured to the distal cage (which are discussed in greater detail below) and are configured to fix the adjustment screw longitudinally relative to the distal cage. In such embodiments, the distal end of the adjustment screw includes a radial groove or flange to engage the rods. In some embodiments, one or more ends of the rods may serve as the lateral projections that slide along the angled slots. In some embodiments, the rods may be integral to the distal cage.

Whether threadingly engaged with the proximal or distal cage, rotation of the adjustment screw translates the distal cage longitudinally causing its distal end to press against inner surface of the superior and inferior shells. Alternatively, or additionally, lateral projections on the distal cage slide along the slots on the side walls of the superior and inferior shells to press the shells apart. Because the proximal ends of both the superior and inferior shells are pivotally engaged to the proximal end of the proximal cage, the expansive force applied to the shells by the distal cage causes the shells to open in a clamshell fashion so as to achieve lordosis when inserted between two vertebrae in a spine.

In some embodiments, the distal end of the distal cage includes sloped, tapered, rounded, and/or ramped surfaces. In some embodiments, rods that may have a lower coefficient of friction than the distal cage material are inserted or secured at distal locations on the distal cage as to be a point of contact between the distal cage and the respective inner surfaces of the superior and inferior shells. In some embodiments, the rods are the primary or only point of contact.

In some embodiments, the expandable interbody includes one or more retention prongs configured to extend or deploy from the interbody when it is expanded. The prongs are sharp and may either embed themselves in the superior and inferior vertebrae or at least resist movement of the interbody. In some embodiments, proximal ends of the retention prongs are secured to or form an integral part of the rods that are set in or pivotally secured to the distal cage. Translation of the distal cage forces the prongs out of respective holes or windows in the superior and inferior shells that may be positioned distally.

According to some embodiments, the edges of the superior and inferior shells are configured to meet each other to fully or at least partially enclose the control assembly when the interbody is in a collapsed state. In some embodiments, the edge of one shell includes projections, and the edge of the other shell includes corresponding depressions configured to receive the projections to thereby provide additional rigidity to the interbody when in the collapsed state. In some embodiments, the superior and inferior shells at least partially nest within each other when in the collapsed state. In some embodiments, the side walls of the proximal and distal cages are sized and configured to contact inner surfaces of the superior and inferior shells to provide stability or rigidity not only in the collapsed state but also in the expanded state.

According to some embodiments, the expandable interbody comprises one or more metals, such as steel, cobalt, cobalt-chrome, titanium, or alloys thereof. In some embodiments, the interbody further includes one or more polymers, such as polyether ether ketone (PEEK). In some embodiments, at least a portion of the interbody includes a porous material, such as a porous metal (e.g., one or more layers of porous titanium).

Also disclosed herein are embodiments of an inserter for use with the expandable interbody. The inserter can include (1) a handle portion with an extension having a cannula extending from a proximal end of the handle to a distal end of the extension, (2) an engagement portion on the distal end of the extension that includes an engagement mechanism for engaging an expandable interbody and one or more counter torque extensions to prevent the engagement mechanism from rotating the interbody, and (3) an expansion tool extending from the proximal end of the cannula to the distal end of the cannula so as to be inserted into the expandable interbody and engage with and activate the adjustment screw.

Some embodiments of an inserter include an expansion indicator that may be located on the handle or on the extension portion. The expansion indicator provides a visual indication to a user as to the degree to which the interbody has been expanded when in situ. In some embodiments, the interbody can be "pre-expanded," meaning that in its collapsed state, the superior and inferior shells are at least partially expanded so as to achieve greater expansion when in the expanded state. In such embodiments, different expansion tools may be used each one corresponding to a different degree of pre-expansion so as to work with the expansion indicator to provide an accurate indication of the degree of expansion.

Also disclosed herein are methods of implanting and expanding an expandable interbody. Such methods include (1) using an inserter to position the interbody—which may be in a collapsed or pre-expanded state—in an intervertebral disc space, (2) expanding the interbody by rotating a control knob on the inserter to expand the interbody, and (3) releasing or disengaging the expanded interbody from the inserter. Some embodiments further include a step of injecting or inserting a bone growth material into the interbody, which can be achieved through the inserter or using a separate device. In embodiments where the inserter is used, a portion of the inserter is removed to allow the bone growth material to be injected or inserted through the inserter into the interbody.

BRIEF DESCRIPTION OF THE DRAWINGS

The embodiments set forth in the drawings are illustrative and exemplary in nature and are not intended to limit the subject matter defined by the claims. The following detailed description of the illustrative embodiments can be better understood when read in conjunction with the following drawings wherein like structure is indicated with like reference numerals and in which:

DETAILED DESCRIPTION

The present disclosure relates to expandable and/or dynamic interbody (between adjacent vertebrae), intravertebral-body (inside the vertebrae), and/or spinal stabilization devices that can be used as interbody fusion cages or devices, interbody bodies/body stabilization devices, and/or the like (collectively hereinafter, spinal device(s)) for providing support, stabilization, and/or promoting bone growth between or inside vertebrae that have been destabilized or otherwise damaged due to injury or illness. Particularly, the present disclosure provides various versions of dynamic (expandable and/or expandable and retractable) interbody devices that are usable in a spinal column of a human and that can achieve or promote proper lordosis.

Figure 1:
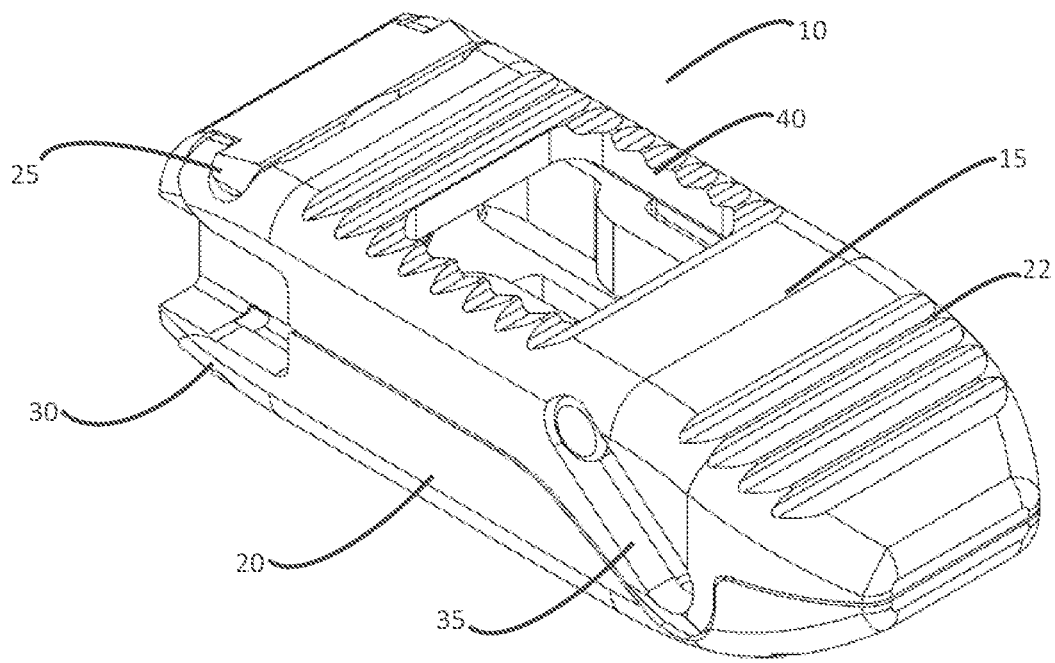
FIG. 1 is a perspective frontal view showing an embodiment of an expandable interbody in a collapsed or unexpanded state.

FIG. 1 illustrates a representative dynamic spinal interbody device or expandable implant or interbody 10. FIG. 1 is a perspective frontal view of interbody 10 in an unexpanded or collapsed state. Interbody 10 includes superior shell 15 and inferior shell 20. A superior surface of superior shell 15 is intended to contact and support an inferior surface of a first vertebral body. Similarly, an inferior surface of inferior shell 20 is intended to contact and be supported by a superior surface of a second vertebral body. In this illustrated embodiment, superior shell 15 and inferior shell 20 include ridges or teeth 22 configured to resist or minimize movement of interbody 10 after being placed in the intervertebral space between the first and second vertebrae. Some embodiments further or alternatively include a roughened surface that can be achieved with a coating and/or a surface treatment. The first and second vertebrae can represent, for example, L1-L2, L2-L3, L3-L4, L4-L5, or even L5-S1 of a human spine. Though interbody 10 could alternatively be used in the thoracic or even the cervical spine.

Both superior shell 15 and inferior shell 20 are configured to hinge at their respective proximal ends at superior hinge point 25 and inferior hinge point 30. The respective distal ends of superior shell 15 and inferior shell 20 are shown as being tapered or shaped like the nose of a bullet. In some embodiments, the distal end of interbody 10 is not tapered at all, though tapering of the distal end can aid in the insertion of interbody 10 into the intervertebral disc space. In some embodiments, such tapering can consist of relatively straight but angled surfaces, and in some embodiments, such tapering can include one or more curves.

FIG. 1 illustrates that the edges of superior shell 15 and inferior shell 20, when in an unexpanded state, meet each other so as to form a closed shell. It is seen that superior shell 15 and inferior shell 20 comprise both a horizontal surface and respective side walls. FIG. 1 shows that one side wall of superior shell 15 has an angled slot 35. In this illustrated embodiment, a similar slot is found in the opposing side wall of inferior shell 20 on the side of interbody 10 not visible in FIG. 1. These angled slots extend through superior shell 15 and inferior shell 20, though in some embodiments, the slots do not extend completely through the shells and instead comprise channels or depressions formed on the inner surface of the shells.

Although not shown, in some embodiments, the edges of the side walls can include projections and corresponding holes or slots for receiving the projections. For example, the inferior surface of the side walls of superior shell 15 can include one or more projections that are received, when in the unexpanded state, by corresponding holes in the superior surface of the side walls of inferior shell 20. Such a configuration can increase the structural integrity or stability of interbody 10 when in an unexpanded state, which can be particularly useful when interbody 10 is inserted into the intervertebral space and may be subject to compaction forces to be positioned correctly.

FIG. 1 also illustrates that superior shell 15 includes graft window 40. A similar graft window is found in inferior shell 20. These graft windows allow for bone growth through interbody 10 after it has been implanted. These graft windows also allow materials that induce or promote bone growth to be inserted or pushed into interbody 10 and at least partially flow out of interbody 10 to potentially contact and interact with the bony surfaces of the superior and inferior vertebral bodies. In some embodiments, interbody 10 includes only one or no graft windows. In some embodiments, interbody 10 includes three or more graft windows, which may be located in locations other than those illustrated in FIG. 1. In some embodiments, as is discussed in greater detail below, interbody 10 can achieve in-growth of new bone instead of or in addition to through growth.

Figure 2:
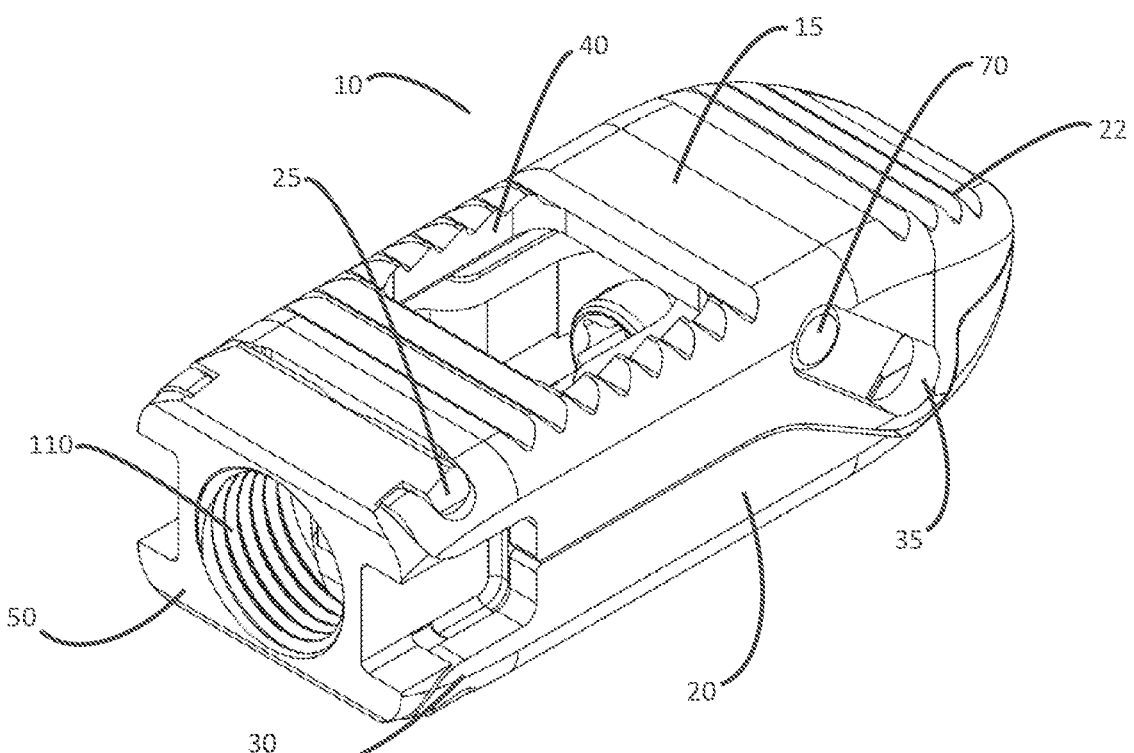
FIG. 2 is a perspective rear view of the embodiment of FIG. 1 in the unexpanded state.

FIG. 2 is a rear perspective view of interbody 10. This perspective illustrates that interbody 10 includes proximal cage 50—discussed in greater detail below. FIGS. 1 and 2 illustrate that superior hinge point 25 and inferior hinge point 30 comprise a combination of a set of lateral protrusions from proximal cage 50 that engage with respective proximal hooks on superior shell 15 and inferior cage 20. Such a configuration allows superior cage 15 and inferior cage 20 to pivot at their respective proximal ends. In some embodiments, such movement can be achieved using a pin extending through proximal cage 50 to as the pivot point. However, the use of the lateral protrusions and hooks shown in the figures not only reduces the number of components but also allows for internally threaded bore 110 to be larger than might be the case if one or more pins are used for superior hinge point 25 and/or inferior hinge point 30.

Figure 3:
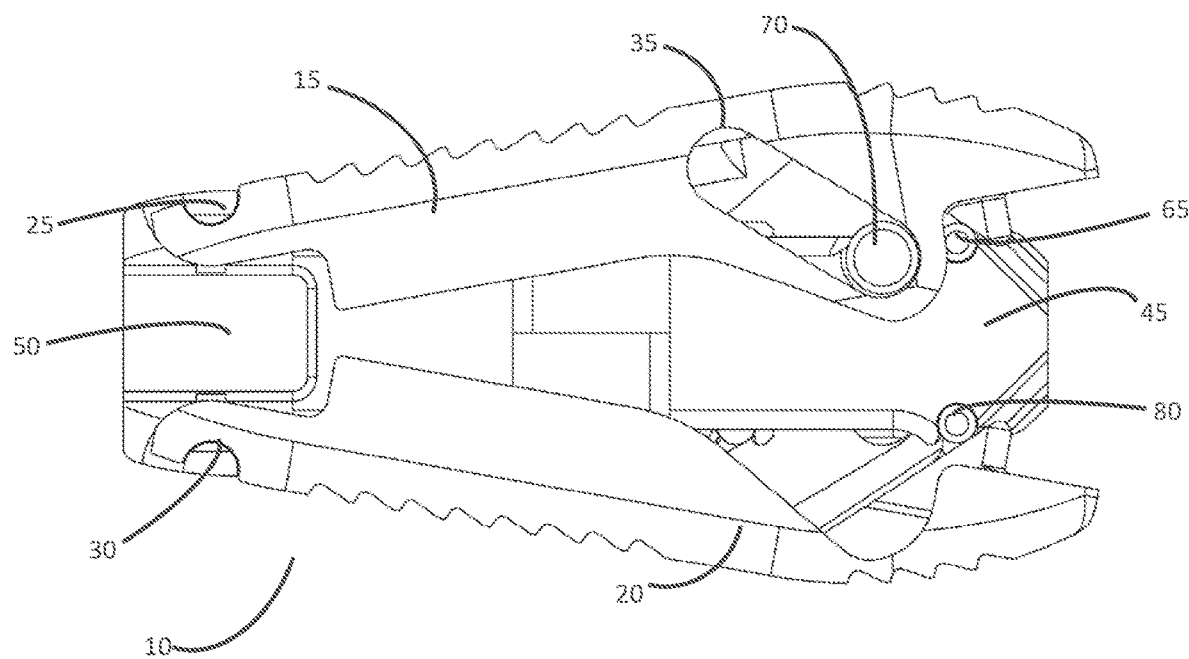
FIG. 3 is a lateral view of the embodiment of FIG. 1 in an expanded state.
Figure 8:
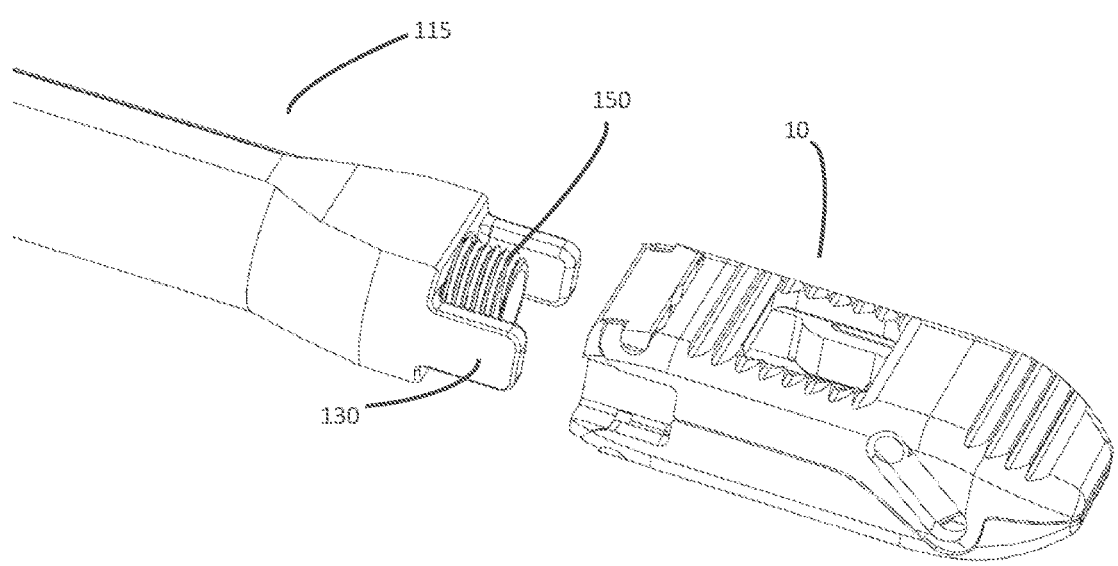
FIG. 8 is a perspective view of the distal portion of the inserter of FIG. 7 disengaged from the expandable interbody of FIG. 1.

FIG. 2 illustrates that proximal cage 50 includes threaded bore 110 on its proximal end configured to threadingly receive an inserter as illustrated in FIG. 8. In some embodiments, the inserter engages interbody 10 with any number of other suitable engagement means, such as an inserter tube with one or more protruding lobes that insert into a similar keyed shaped hole that allows passage of the tube through the proximal cage and then partially rotate to secure the lobes to the inner wall FIG. 3 illustrates interbody 10 in an expanded state in which the distal ends of superior shell 15 and inferior shell 20 are spaced apart while the respective proximal ends pivot about superior hinge point 25 and inferior hinge point 30. In this expanded state and in the perspective view of FIG. 3, it can be seen that interbody 10 includes a distal cage 45, a proximal cage 50, and an adjustment screw 55. These elements are sometimes referred to herein as the control assembly. Proximal cage 50 and distal cage 45 are configured to interlock with each other—as illustrated in more detail in FIG. 4—so as to allow relative movement or translation between them along a longitudinal axis, which is the longitudinal axis of adjustment screw 55, which extends through an opening in proximal cage 55 and threadingly engages with a threaded bore found on the distal end of distal cage 45.

In the illustrated embodiment, expansion of interbody 10 from the unexpanded state to the expanded state is achieved when adjustment screw 55 is rotated so as to displace distal cage 45 relative to proximal cage 50. And because superior hinge point 25 and inferior hinge point 30 are located at the proximal end of proximal cage 50, the longitudinal displacement of distal cage 45 applies a force to one or more interior surfaces of superior shell 15 and inferior shell 20 causing the respective distal ends of the shells to open in a clamshell fashion.

According to some embodiments, the distal end of proximal cage 50 comprises a threaded bore that threadingly engages with adjustment screw 55. In such embodiments, distal cage 45 does not have a threaded bore but is configured to receive the force applied by the distal end of adjustment screw 55 when it is advanced through proximal cage 50. The force applied to distal cage 45 by adjustment screw 55 causes distal cage 45 to translate longitudinally relative to proximal cage 50, thereby causing the distal ends of superior shell 15 and inferior shell 20 to move apart. Threading adjustment screw 55 with the distal end of proximal cage 50 can, in some embodiments, reduce the amount of friction between adjustment screw 55 and interbody 10 such that less force is required to rotate adjustment screw 55. Moreover, tapering the distal end of adjustment screw 55 can, in some embodiments, further reduce the friction between adjustment screw 55 and interbody 10.

The embodiment illustrated in FIG. 3 includes a tapered distal end on distal cage 45. In some embodiments, the tapered distal end comprises equally angled surfaces 60. In some embodiments, a rounded or cylindrical surface is included near the distal end of distal cage 45 along with angled surface 60 or in lieu of angled surface 60. In the embodiment illustrated in FIG. 3, the cylindrical surface comprises a pin or rod 65 positioned in a cutout on the superior face of distal cage 45. A corresponding pin or rod may be placed in a cutout on the inferior face of distal cage 45, though some embodiments utilize only a single rod. In some embodiments, the one or more rods are integral to distal cage 45. In some embodiments, the rounded or cylindrical surface comprises a material having a lower coefficient of friction than the material that comprises angled surface 60 or the rest of distal cage 45.

FIGS. 1-4 illustrate that distal cage 45 includes a lateral projection 70 configured to slide in angled slot 35. Comparing the expanded state of FIG. 3 to the unexpanded stated of FIGS. 1 and 2, it can be seen that lateral projection 70 moves from a proximal end to a distal end of angled slot 35. Distal cage 45 includes a second lateral projection on the opposite side of distal cage 45, the side not visible in FIG. 2. The second lateral projection, similar to lateral projection 70, is configured to slide in the angled slot found in the side wall of inferior shell 20. The exact angle of angled slot 35 in superior shell 15 (and corresponding angled slot 85 in inferior shell 20) can be selected to achieve a desired lordosis angle and/or a desired rate of expansion for each turn of adjustment screw 55. In some embodiments, the angle of angled slot 35 is distinct from the angle of angled slot 85 of inferior shell 20 such that rotation of adjustment screw 55 to expand interbody 10 results in uneven expansion of each lateral side of interbody 10.

According to some embodiments, one or both of rod 65 and/or rod 80 serves as lateral projection 70 and/or the corresponding lateral projection on the opposite side of distal cage 45. For example, rod 65 and/or rod 80 need only be extended beyond what is illustrated to able to extend into the side walls of superior cage 15 and/or inferior cage 20. Such a configuration can result in fewer components, which not only has the potential to affect the cost of interbody 10 but also its manufacturability and structural integrity.

In some embodiments, one or both of superior shell 15 and inferior shell 20 includes a porous material, which can be metallic or polymeric or a combination of the two. In some embodiments, one or both of superior shell 15 and inferior shell 20 include a cutout or depression in their exterior surface(s) to accommodate a layer of porous material that is configured to occupy the cutout or depression in the exterior surface(s). In some embodiments, the layer of porous material is simply affixed or secured to the superior and/or inferior surface of interbody 10, and no cutout is used or required. In some embodiments, the porous material is one or more layers of a porous sheet, such as one or more layers of a sheet of porous titanium. The layer(s) of porous titanium can be diffusion bonded to the exterior surface(s) of superior shell 15 and/or inferior shell 20. In some embodiments, the porous material surrounds, is adjacent to, or replaces one or both of the graft windows. In some embodiments, the porous material is positioned on one or more side walls in addition to or instead of on a superior or inferior surface of interbody 10.

Figure 4:
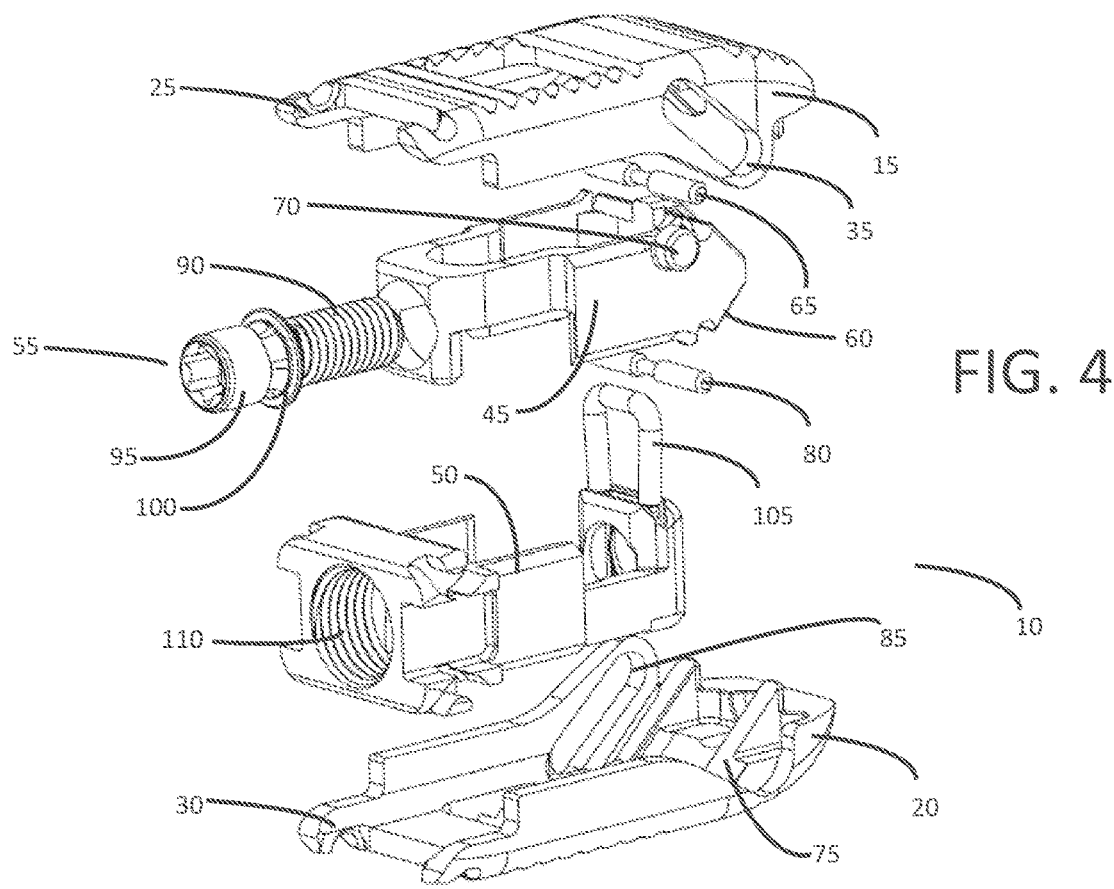
FIG. 4 is an exploded rear view of the embodiment of FIG. 1.

FIG. 4 is an exploded view of the embodiment of FIG. 1 where some aspects of the various components of interbody 10 are better visualized. For example, slot 85 in the side wall of inferior shell 20 is visible as well as the interlocking nature of the respective structures of proximal cage 50 and distal cage 45. Also illustrated in FIG. 4 is ramped surface 75 of inferior shell 20. In this illustrated embodiment, both inferior shell 20 and superior shell 15 include respective ramped surfaces toward the distal end of the shells. As explained above, expandable interbody 10 expands when adjustment screw 55 longitudinally displaces distal cage 45 away from or relative to proximal cage 50. This displacement of distal cage 45 causes the distal portion of distal cage 45 to press against at least one of superior shell 15 and inferior shell 20. In some embodiments, the tapered end or angled surface 60 of distal cage 45 (and possibly the corresponding angled surface on the inferior side of distal cage 45) presses against and slides along one or both of the ramped surfaces of superior shell 15 and inferior shell 20. In some embodiments, the same movement is achieved by virtue of rod 65 and/or rod 80 pressing against and sliding along one or both of the ramped surfaces of superior shell 15 and inferior shell 20. In some embodiments, the longitudinal displacement of distal cage 45 causes lateral projection 70 to slide along slot 35 (and possibly the corresponding lateral projection on the opposite side of distal cage 45 sliding along slot 85 found in one side wall of inferior shell 20), thereby causing the distal ends of superior shell 15 and inferior shell 20 to separate from each other.

In some embodiments, the mechanism by which expandable interbody 10 expands is a combination of all three structural relationships (tapered end of distal cage 45, rods 65 and 80, and lateral projection 70), a combination of just two of these structural relationships, or just one of the structural relationships.

FIG. 3 further illustrates that adjustment screw 55, in this embodiment, includes threaded portion 90, head 95, and flange 100 positioned between head 95 and threaded portion 90. When assembled, adjustment screw 55 extends through an opening in the distal portion of proximal cage 50, and threaded portion 90 threadingly engages a threaded bore in distal cage 45. The longitudinal position of adjustment screw 55 is fixed relative to proximal cage by virtue of pin 105. In this illustrated embodiment, pin 105 slips into a slot on the distal portion of proximal cage 50. Pin 105 includes prongs or extensions that engage flange 100 of adjustment screw 55 to maintain adjustment screw 55 in a longitudinally fixed orientation relative to proximal cage 50. In some embodiments, flange 100 is a groove or depression configured to receive pin 105. In some embodiments, flange 100 is accompanied by a groove or depression. In some embodiments, pin 105 comprises a cylindrical shape and engages with adjustment screw 55 along only one side of adjustment screw 55.

The components illustrated in FIG. 4 can be formed of any suitable material, such as one or more metals or one or more polymers. Such materials include titanium, steel, cobalt, gold, platinum, silver, iridium, tantalum, tungsten, and alloys thereof, polyvinylidene fluoride, polyethylene, polypropylene, polydimethylsiloxane, parylene, polyamide, polytetrafluoroethylene, polymethylmethacrylate, polyimide, PEEK, and polyurethane. In some embodiments, one or more of the components illustrated in FIG. 4 includes a porous material. Porous materials can include porous metals as well as porous polymers or a mixture of the two. For example, in some embodiments, one or more components includes or is manufactured from porous titanium. In some embodiments, the porous titanium comprises layered sheets of porous titanium that have been diffusion bonded to each other to form a unitary whole. In some embodiments, one or more of superior shell 15, inferior shell 20, distal cage 45, or proximal cage 50 is manufactured from or includes layered sheets of porous titanium that have been diffusion bonded to each other. When such porous components are used, this allows for bone growth through or into interbody 10 itself rather than just through graft windows.

An inserter (see FIG. 7) suitable for use with expandable interbody 10 will have an engagement means (see FIG. 8) that engages a proximal portion of proximal cage 50, and the insert will include an adjustment tool portion that extends through threaded bore 110 to mate with head 95 of adjustment screw 55 so as to rotate adjustment screw 55 and thereby expand or collapse interbody 10.

Figure 5A:
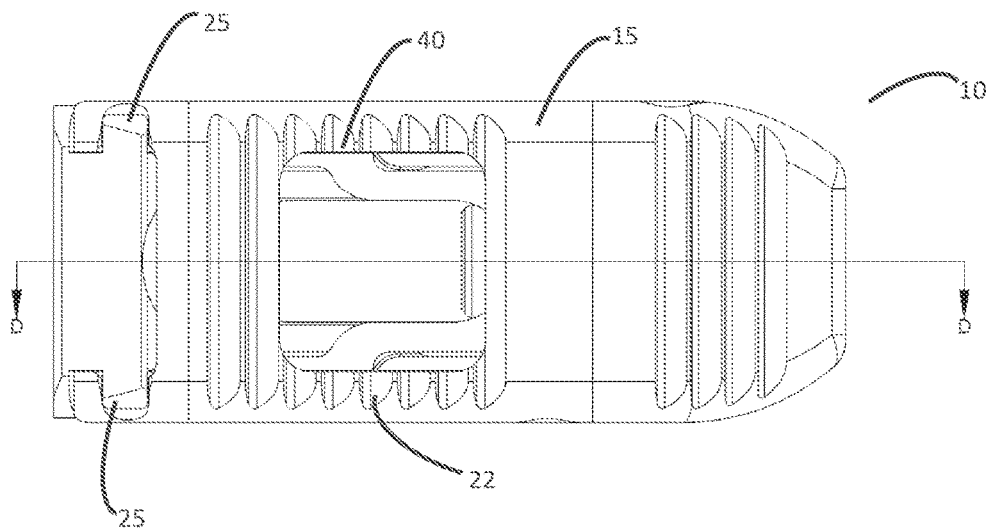
FIG. 5A is a superior view of the expandable interbody of FIG. 1 in the unexpanded state.
Figure 5B:
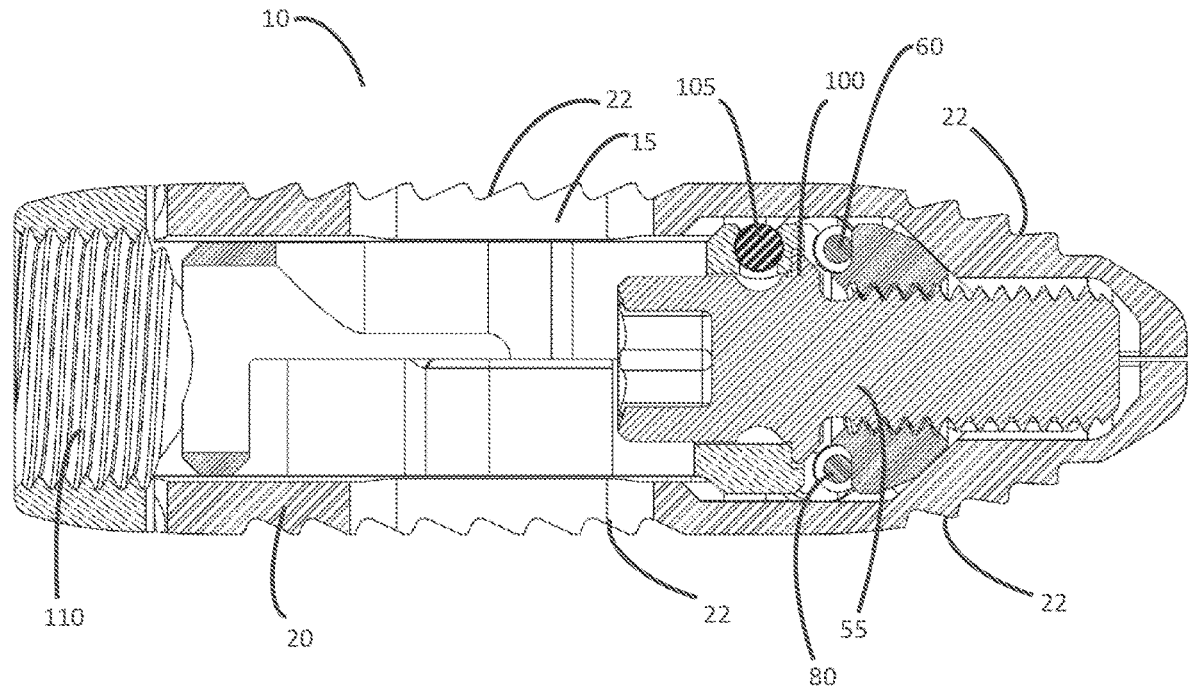
FIG. 5B is a lateral cross-sectional view of the expandable interbody of FIG. 1 in the unexpanded state taken along line D-D shown in FIG. 5A.
Figure 6A:
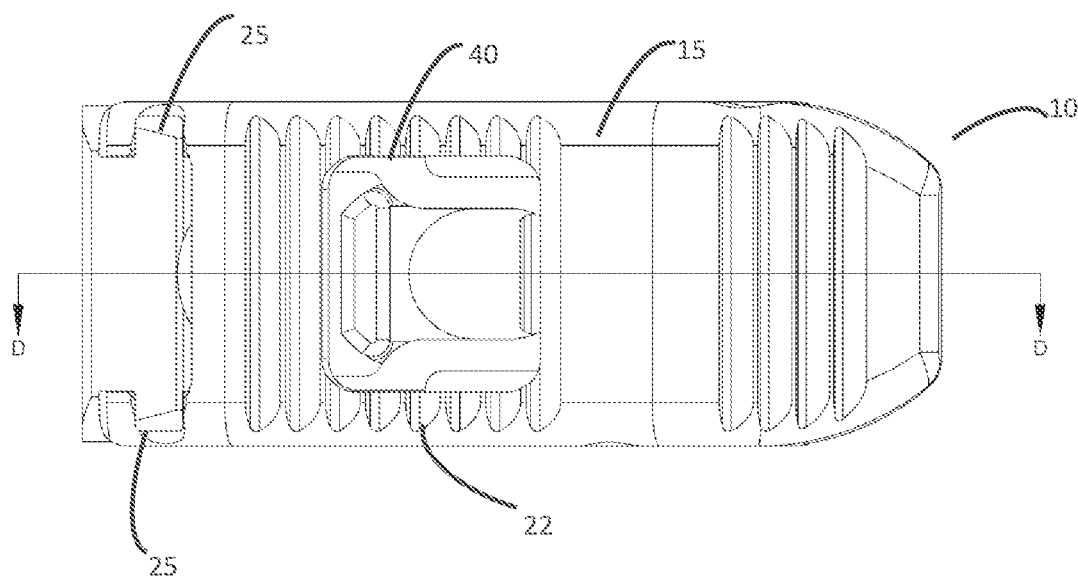
FIG. 6A is a superior view of the expandable interbody of FIG. 1 in the expanded state.
Figure 6B:
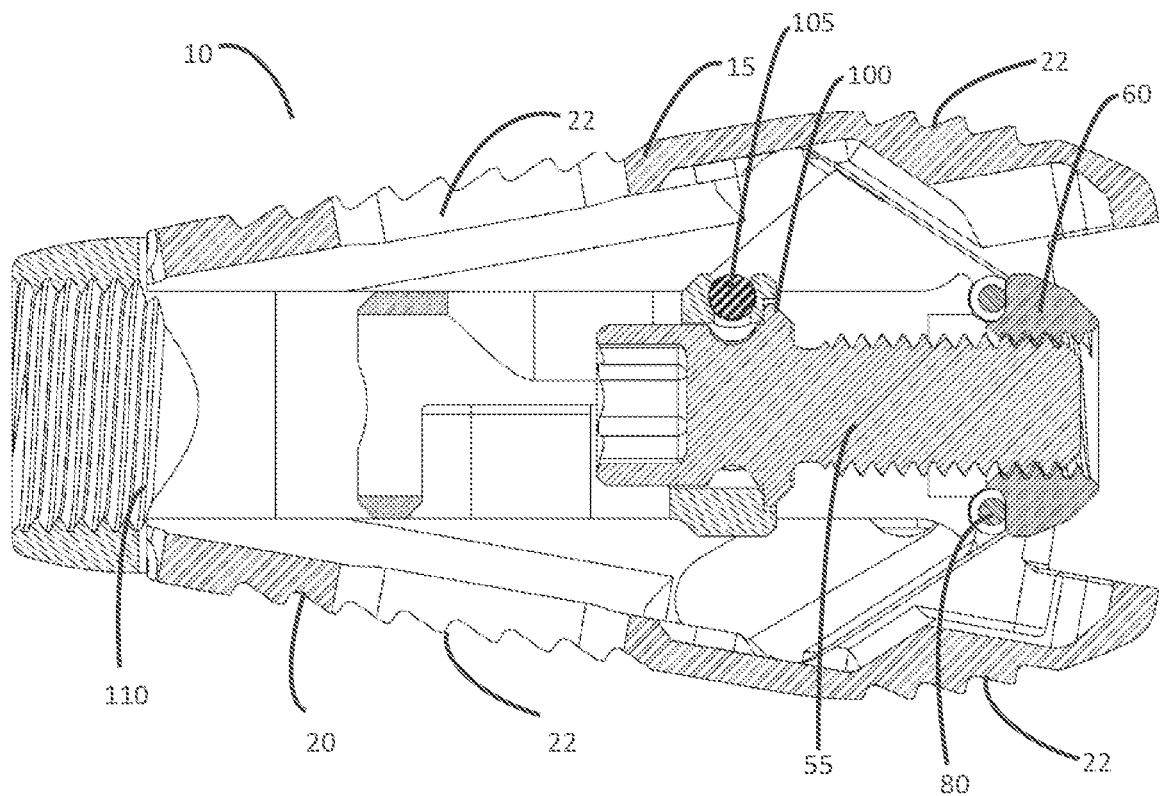
FIG. 6B is a lateral cross-sectional view of the expandable interbody of FIG. 1 in the expanded state taken along line D-D shown in FIG. 6A.

FIGS. 5 and 6 are cross-sectional views of expandable interbody 10 in both the unexpanded state (FIG. 5) and the expanded state (FIG. 6). These figures illustrate the function of adjustment screw 55 as well as how distal cage 45 interacts with superior shell 15 and inferior shell 20 to force the distal ends of the two shells apart to take interbody 10 from the unexpanded state to the expanded state.

FIGS. 5 and 6 also illustrate how graft window 40 in superior shell 15 has a corresponding graft window in inferior shell 20 and that the two graft windows along with openings in the respective structures of distal cage 45 and proximal cage 50 (see FIG. 4) create an opening through the entire depth of interbody 10 to allow for bone through growth.

FIG. 5 illustrates superior shell 15 and inferior shell 20 of interbody 10 as defining separate planes that are substantially parallel when interbody 10 is in the unexpanded state. In the unexpanded state, the respective superior and inferior surfaces of superior shell 15 and inferior shell 20 may be substantially parallel, or they may exhibit a slight angle, such as about 0.5°, about 1°, about 1.5°, about 2°, between about 0° and about 1°, between about 0.2° and about 1.2°, or between about 0.5° and about 2°. In some embodiments, the angle between the respective superior and inferior surfaces may be less than about 5°, less than about 4°, less than about 3°, or less than about 2°. According to some embodiments, an initial or pre-expanded angle between the respective superior and inferior surfaces greater than 0° may facilitate a larger angle when in the expanded state.

According to some embodiments, an initial angle is achieved through the design of superior shell 15 and inferior shell 20 rather than or in conjunction with pre-expanding interbody 10. In some embodiments, superior shell 15 and/or inferior shell 20 are thicker toward their respective distal ends. Designing superior shell 15 and/or inferior shell 20 in such a manner can be used to achieve an initial angle of about 1° to about 15° including any angle there between. In some embodiments, the resulting initial angle is at least about 1°, at least about 3° at least about 5°, at least about 7°, at least about 9°, at least about 11°, at least about 13°, less than about 14°, less than about 12°, less than about 10°, less than about 8°, less than about 6°, and/or less than about 4°.

In some embodiments, the internal components of interbody 10 are identical between an embodiment having an initial angle and one that does not. In other words, where one embodiment without an initial angle can achieve an expanded angle of about 20°, the same internal components used in an embodiment with thicker shells that has an initial angle of about 10° may achieve an expanded angle of about 30°.

The length of interbody 10—defined as the distance between the most proximal and the most distal portions of superior shell 15 (or inferior shell 20)—can be any suitable value. In some embodiments, the length is from about 14 mm to about 41 mm including any value there between. In some embodiments, the length of interbody 10 is about 20 mm, about 22.5 mm, about 25 mm, about 27.5 mm, about 30 mm, about 32.5 mm, at least about 20 mm, at least about 25 mm, at least about 30 mm, at least about 35 mm, less than about 40 mm, less than about 37 mm, less than about 33 mm, less than about 27 mm, between about 15 mm and about 25 mm, between about 20 mm and about 30 mm, or between about 25 mm and about 35 mm.

The width of interbody 10—defined as the distance between the outside edge of the respective side walls of superior shell 15 (or inferior shell 20)—can be any suitable value. In some embodiments, the value of the width is selected to provide maximum stability to the superior and inferior vertebrae. In some embodiments, the width is from about 7 mm to about 27 mm including any value there between. In some embodiments, this value is about 8 mm, about 10 mm, about 12 mm, about 14 mm, about 16 mm, about 18 mm, about 20 mm, about 22 mm, about 24 mm, about 26 mm, at least about 7.5 mm, at least about 12.5 mm, at least about 17.5, at least about 22.5, less than about 27 mm, less than about 23 mm, less than about 19 mm, less than about 15 mm, between about 7 mm and about 13 mm, between about 9 mm and about 15 mm, between about 11 mm and about 17 mm, between about 13 mm and about 19 mm, between about 15 mm and about 21 mm, between about 17 mm and about 23 mm, or between about 19 mm and about 25 mm.

FIG. 6 illustrates that the angle between the respective planes defined by superior shell 15 and inferior shell 20 in the expanded state can be from about 4° to about 40° including any value there between. In some embodiments, the angle is about 10°, about 15°, about 20°, about 25°, about 30°, or about 35°. In some embodiments, the angle in the expanded state is at least about 5°, at least about 10°, at least about 15°, at least about 20°, at least about 25°, at least about 30°, between about 5° and about 10°, between about 7.5° and about 12.5°, between about 10° and about 15°, between about 12.5° and about 17.5°, between about 15° and about 20°, between about 17.5° and about 22.5°, between about 20° and about 25°, between about 22.5° and about 27.5°, between about 25° and about 30, or even between about 27.5° and about 32.5°.

Figure 7:
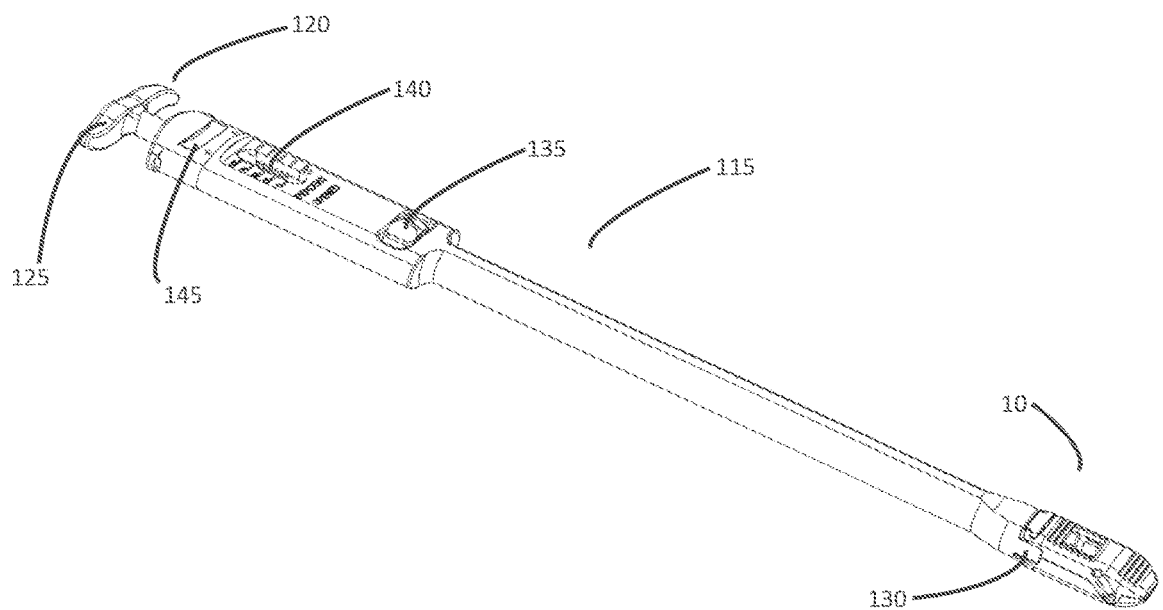
FIG. 7 is a perspective view of an inserter engaged with the expandable interbody of FIG. 1.

FIG. 7 illustrates inserter 115 for use with interbody 10. Inserter 115 includes a distal end configured to engage the proximal end of interbody 10 and a proximal end configured to be handled and manipulated by a user (e.g., a surgeon). Inserter 115 includes expansion tool 120 that includes handle 125 and a rod (not shown). The rod extends through a lumen that runs the length of inserter 115 and extends at least partially beyond the distal end of inserter 115 so as to extend at least partially into interbody 10 when inserter 115 is engaged with interbody 10. The distal end of the rod of expansion tool 120 is configured to engage head 95 of adjustment screw 55. Thus, rotation of handle 125 causes the rod of expansion tool 120 to rotate, which in turn causes adjustment screw 55 to rotate thereby expanding or collapsing interbody 10.

The distal end of inserter 115 includes a threaded engagement portion 150 (see FIG. 8) and lateral extensions 130. Engagement portion 150 is configured to engage with threaded bore 110 of proximal cage 50. Lateral extensions 130 provide a counter torque to the rotation applied by engagement portion 150 so as to hold interbody 10 in place while engagement portion 150 is rotated to cause inserter 115 to either engage with or disengage from interbody 10. Manipulation of engagement portion 150 is accomplished by rotating engagement knob 135 located toward the proximal end of inserter 115.

FIG. 8 illustrates that engagement portion 150 is hollow. This allows expansion tool 120 to pass through engagement portion 150 and extend into interbody 10 passing through the proximal portion of proximal cage 50 to engage with adjustment screw 55. Although not illustrated, expansion tool 120 can be removed from inserter 115 to allow for biologics or bone-growth-promoting materials to be injected into interbody 10 through inserter 115.

Additionally, in some embodiments, lateral extensions 130 come into contact with the respective proximal edges of the side walls of superior shell 15 and inferior shell 20 particularly when interbody 10 is in the unexpanded state. Such a configuration allows inserter 115 to distribute an insertion or compaction force to the shell portions rather than have proximal cage 50 receive the entire insertion force.

The proximal portion of inserter 115 includes surfaces that facilitate the use of inserter 10 to insert, extract, expand, or collapse interbody 10. In the embodiment illustrated in FIG. 7, the proximal portion of inserter 115 includes flat surfaces that are easy for a surgeon to grip. The proximal portion may also include expansion indicator 140 that provides an indication of the amount or degree of expansion of interbody 10. This may be particularly helpful to the surgeon as the expansion may not be visible when interbody 10 has been inserted into the intervertebral space. Moreover, fluoroscopic images are not likely to provide the surgeon with precise information as to the expansion angle achieved in situ. Expansion indicator 140 may provide a percentage value of the expansion. For example, if interbody 10 has been designed to achieve an angle of 20° when fully expanded, expansion indicator 140 will indicate what percentage of that angle has been achieved. When interbody 10 is in its unexpanded state (before being inserted), expansion indicator 140 will show 0% expansion. When interbody 10 has been expanded to about 10°, expansion indicator 140 will show 50% expansion, and when interbody 10 has been expanded to about 20°, expansion indicator 140 will show 100% expansion. In some embodiments, expansion indicator 140 is configured to provide the actual degree or angle of expansion.

According to some embodiments, the unexpanded state of interbody 10 is defined as a configuration where the angle between the superior and inferior planes is greater than 0°. Such a configuration may advantageously allow for a greater degree or angle of expansion for the final expanded state. In some embodiments, the initial angle is between about 0.5° and about 10° including any angle there between. In some embodiments, the initial angle is about 1°, about 1.5°, about 2°, about 2.5°, about 3°, about 3.5°, about 4°, about 4.5°, greater than about 1°, greater than about 3° less than about 9°, less than about 7°, between about 0.5° and about 3.5°, between about 2.5° and about 5.5°, between about 4.5° and about 7.5°, between about 6.5° and about 9.5°.

As discussed above, rotation of expansion tool 120 not only expands interbody 10 but, in some embodiments, affects expansion indicator 140 so as to provide a surgeon with an indication of the degree or percentage expansion achieved by interbody 10 when in situ. In some embodiments where interbody 10 comes initially pre-expanded (e.g, where the minimum angle is greater than 0°), expansion tool 120 communicates with expansion indicator 140 to provide such an indication of pre-expansion. For example, a different expansion tool 120 may be provided for each degree or percentage of pre-expansion. In other words, where interbody 10 comes with 1° pre-expansion as well as 5° pre-expansion, one specific expansion tool 120 is used for each so that when inserter 115 is coupled to the interbody with 1° of pre-expansion, that fact is communicated by expansion tool 120 to expansion indicator 140. When using the interbody with 5° of pre-expansion, a different expansion tool 120 is used. For example, if interbody 10 is initially pre-expanded to 5° and is capable of achieving an expanded state of 25°, then expansion tool 120 is configured to cause expansion indicator 140 to show the initial percentage of expansion as 20%. Thus, when the surgeon inserts interbody 10, she is reminded by the expansion indicator 140 that interbody 10 is pre-expanded or comes with an initial degree of expansion greater than 0°. However, in some embodiments, no such pre-expansion is indicated by expansion indicator 140.

Inserter 115 illustrated in FIG. 7 includes a notch toward the proximal end. This notch (and an optional corresponding notch located on the underside of inserter 115) is configured to engage a counter torque instrument (not shown). Such an instrument can be used to hold inserter 115 in place and prevent it from twisting when handle 125 of expansion tool 120 is rotated to expand interbody 10.

Interbody 10 may be surgically implanted in a patient using any number of suitable methods. In some embodiments, a method of implanting interbody 10 includes the initial step of engaging the distal end of inserter 115 to the proximal end of proximal cage 50. This is done by bringing the distal tip of inserter 115 into contact with the proximal end of proximal cage 50 and rotating engagement knob 135, which in turn rotates engagement portion 150 causing the threads of engagement portion 150 to engage the threads of threaded bore 110 in proximal cage 50. Engagement knob 135 is rotated until lateral extensions 130 are fully advanced into the respective slots on the proximal end of interbody 10 formed in the proximal end of proximal cage 50 as well as in the proximal ends of the respective side walls of superior shell 15 and inferior shell 20. With inserter 115 engaged with interbody 10, adjustment tool 120 can be inserted through inserter 115 to bring its distal end into engagement with adjustment screw 55. In some embodiments, expansion tool 120 is already in place in inserter 115 before inserter 115 is engaged with interbody 10.

Interbody 10 is then positioned in the intervertebral disc space and positioned as desired. Positioning interbody 10 in a desired location can be achieved using fluoroscopy. To this end, one or more of the components of interbody 10 can be at least partially radiopaque. In some embodiments, interbody 10 includes one or more radiopaque markers whose primary purpose is to aid in proper positioning of interbody 10 in the intervertebral disc space. In some embodiments, expansion tool 120 is not inserted through inserter 115 until interbody 10 has been properly positioned in the intervertebral disc space. In embodiments where interbody 10 is positioned prior to insertion of expansion tool 120, the proximal end of inserter 115 can be constructed to receive and withstand hammer blows that may be required to properly position interbody 10.

With interbody 10 properly positioned, expansion tool 120—which may need to be inserted through inserter 115 at this stage—is rotated to cause adjustment screw 55 to rotate, thereby causing distal cage 45 to move longitudinally relative to proximal cage 50. Movement of distal cage 45 away from proximal cage 50 applies an outward pressure on superior cage 15 and inferior cage 20. In some embodiments, this outward pressure comes from lateral projection 70 (and the corresponding lateral projection on the opposite side of distal cage 45) sliding along angled slot 35 and angled slot 85, respectively. In some embodiments, this outward pressure comes from the tapered distal end of distal cage 45 pressing against sloped surfaces on the interior of superior cage 15 and inferior cage 20. In some embodiments, this outward pressure comes from rods 65, 80 pressing against sloped surfaces on the interior of superior cage 15 and inferior cage 20. In some embodiments, this outward pressure comes from a combination of two or more of these structural interactions.

Interbody 10 is expanded by continuing to rotate expansion tool 120 until a desired amount of expansion is achieved. The amount of expansion can be observed using expansion indicator 140, which indicates the amount of expansion in degrees of expansion or percent expansion or any other suitable manner.

Once the desired amount of expansion is achieved, expansion tool 120 is removed from inserter 115. In some embodiments, biologics or materials that promote bone growth are then injected into interbody 10 by injecting them through the cannulated structure of inserter 115. In some embodiment, such materials are injected into interbody 10 or the space surrounding interbody 10 after inserter has been disengaged from interbody 10. Disengagement is achieved by turning engagement knob 135 until the distal tip of inserter 115 can be freely withdrawn from the surgical space without affecting the positioning of interbody 10.

Figure 9:
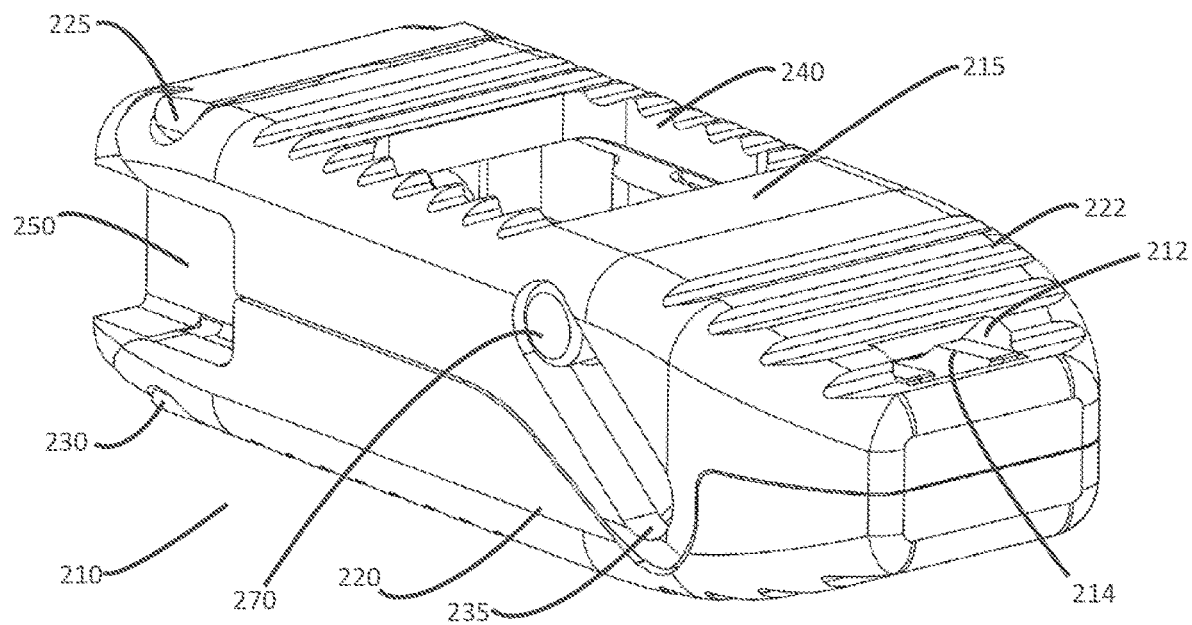
FIG. 9 is a perspective frontal view showing another embodiment of an expandable interbody in a collapsed or unexpanded state.

FIG. 9 illustrates an alternative embodiment of an expandable interbody 210 that includes superior shell 215 and inferior shell 220. Many aspects of interbody 210 are similar to the aspects of interbody 10 (including superior hinge point 225, inferior hinge point 230, proximal cage 250, lateral projection 270, angled slot 235, teeth 222, and graft window 240); however, superior shell 215 and inferior shell 220 each include openings in the superior and inferior surfaces, respectively, toward the distal end of interbody 210. In the perspective shown in FIG. 9, only superior opening 212 is visible, though this embodiment includes a corresponding opening in inferior shell 220. In some embodiments, only one shell has such an opening.

Figure 10:
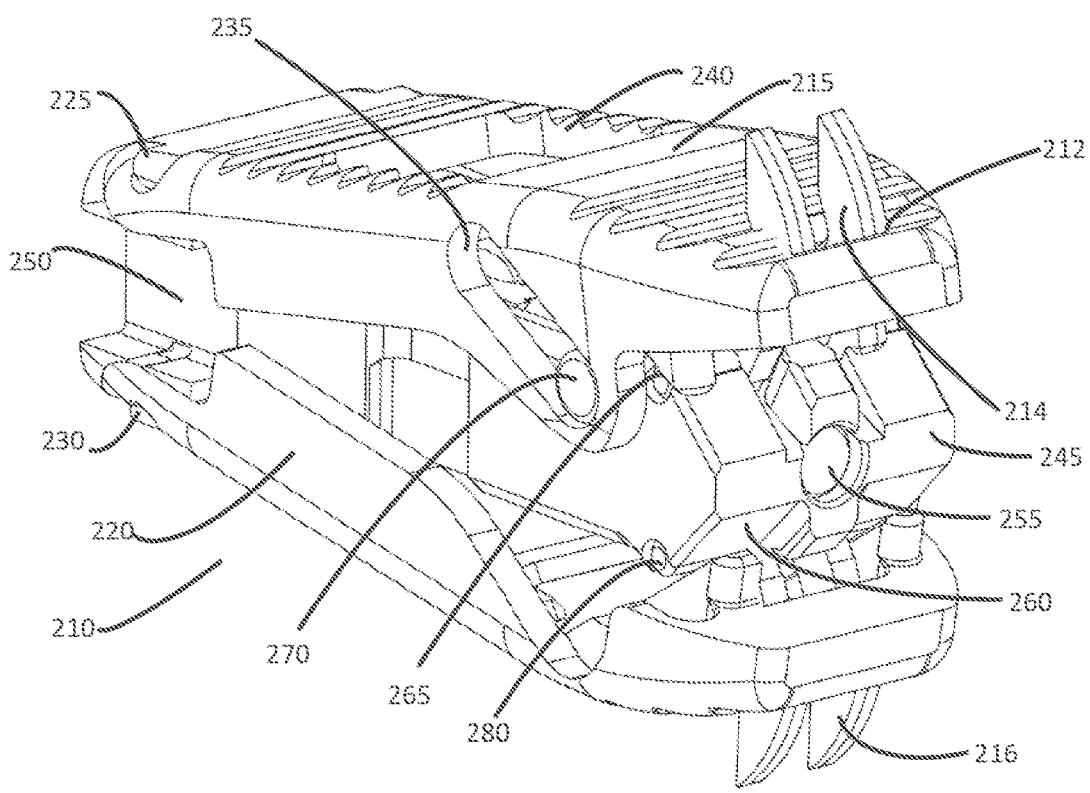
FIG. 10 is a perspective frontal view of the embodiment of FIG. 9 in an expanded state.

FIG. 10 illustrates that when interbody 210 is expanded (by virtue of angled slopes 260 pressing against the inside surfaces of superior shell 215 and inferior shell 220 and/or lateral projection 270 sliding along angled slot 235 along with the not-shown lateral projection sliding along angled slot 285 and/or rods 265, 280 sliding along internal ramped surfaces of superior shell 215 and inferior shell 220), not only do the distal ends of superior shell 215 and inferior shell 220 separate in a clamshell fashion to engage with superior and inferior vertebral bodies, but retention prongs extend through the openings found in the superior shell 215 and inferior shell 220 so as to prevent, limit, or mitigate movement or migration of interbody 210 in the intervertebral space. As with interbody 10, interbody 210 includes superior rod 265 and inferior rod 280; however, in this embodiment, superior rod 265 serves as the point of connection and hinge point for superior retention prong 214 that extends through superior opening 212 when interbody 210 is expanded. Correspondingly, inferior rod 80 serves as the point of connection and hinge point for inferior retention prong 216 that extends through an inferior opening. Some embodiments include only a single deployable retention prong. In some embodiments, the retention prongs are integral to the rods. In some embodiments, the retention prongs pivot freely about the rods. The longitudinal translation of distal cage 245 distally forces superior retention prong 214 and inferior retention prong 216 to press against and slide along their respective openings so as to extend or deploy from interbody 210. Inversely, a proximal translation of distal cage 245 will retract superior retention prong 214 and inferior retention prong 216 back into interbody 210.

Figure 11:
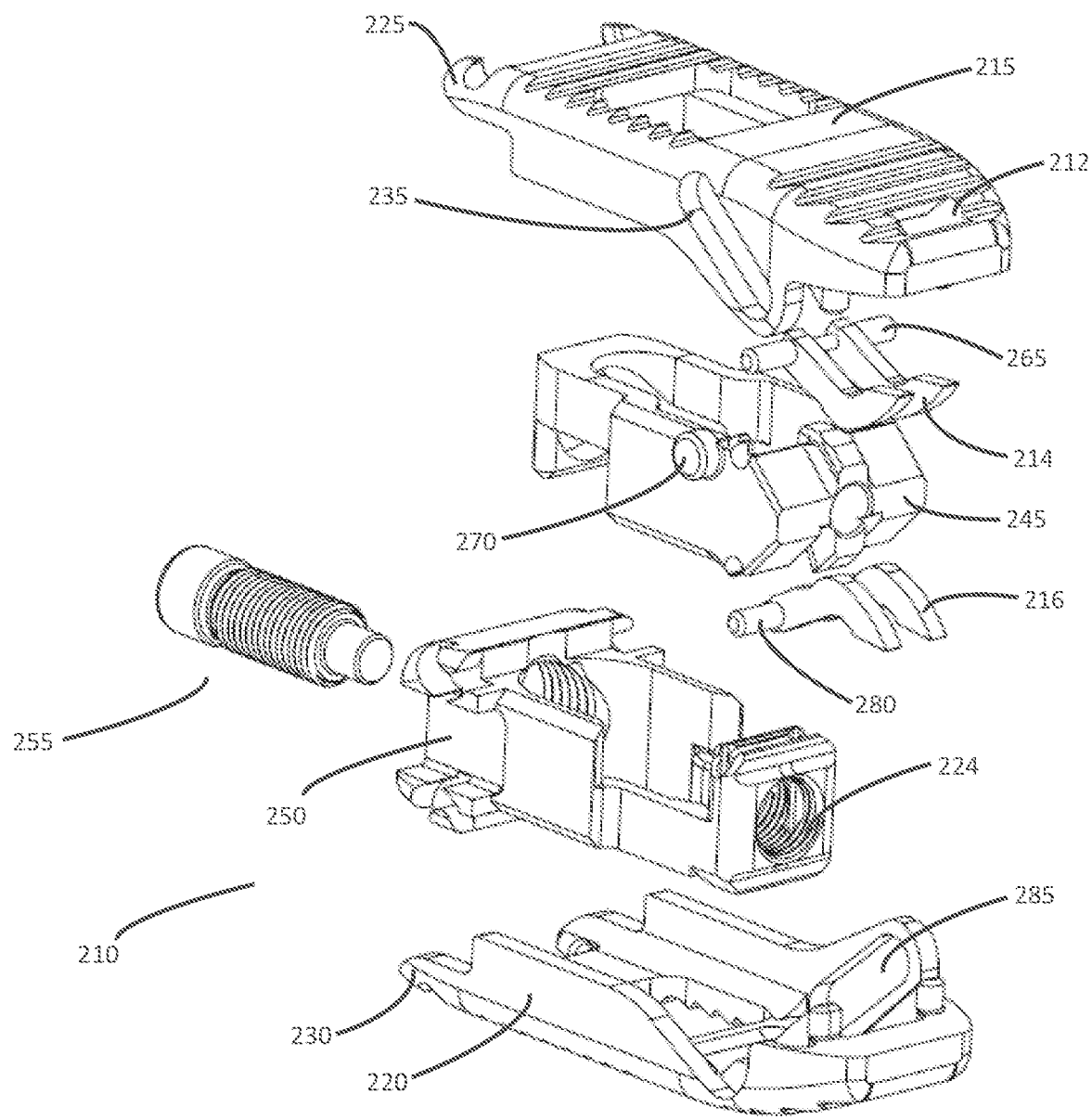
FIG. 11 is an exploded frontal view of the embodiment of FIG. 9.

FIG. 11 is an exploded view of interbody 210 in which it can be seen how superior retention prong 214 and inferior retention prong 216 are connected to superior rod 265 and inferior rod 280, respectively. In some embodiments, the two components are fused, bonded, bound, or adhered together, or they may comprise a unitary piece.

FIG. 11 also illustrates that the distal end of proximal cage 250 includes threaded bore 224. In this embodiment, distal cage 245 does not have a threaded bore. That means that adjustment screw 255 threads into threaded bore 224 and, when rotated, the longitudinal displacement of adjustment screw 255 in the distal direction causes the distal end of adjustment screw 255 (which is shown as being smooth or rounded, though it may also be tapered to reduce friction on some or all of the distal surface of the tip) to press against the distal end of distal cage 245, thereby displacing distal cage 45 and causing distal cage 45 to press open the distal ends of superior shell 215 and inferior shell 220. In some embodiments, the distal end of adjustment screw 255 is held in place within the distal end of distal cage 245 with a pin that allows adjustment screw 255 to freely rotate. In some embodiments, the distal end of adjustment screw 255 is configured to have a snap-fit engagement with distal cage 245.

In some embodiments, a resistance element (not illustrated) can be incorporated into proximal cage 250, preferably at the distal end of proximal cage 250. Such a resistance element may comprise a threaded interior through which adjustment screw 255 is threaded. However, unlike the threaded bore 224 of proximal cage 245, the resistance element is configured to apply at least some resistance to the rotation of adjustment screw 255. Such resistance can prevent expandable interbody 210 from inadvertently collapsing and decreasing in volume during a surgical procedure and/or after surgery. The resistance element can comprise any number of suitable materials, such as a metal (e.g., steel, titanium, alloys thereof, etc.) or a polymer (polyvinylidene fluoride, polyethylene, polypropylene, polydimethylsiloxane, parylene, polyamide, polytetrafluoroethylene, polymethylmethacrylate, silicone, polyimide, PEEK, and polyurethane or a combination thereof). In some embodiments, the resistance element is internally threaded though in some embodiments, the resistance element is not internally threaded but simply applies a frictional force against adjustment screw 255.

Figure 12:
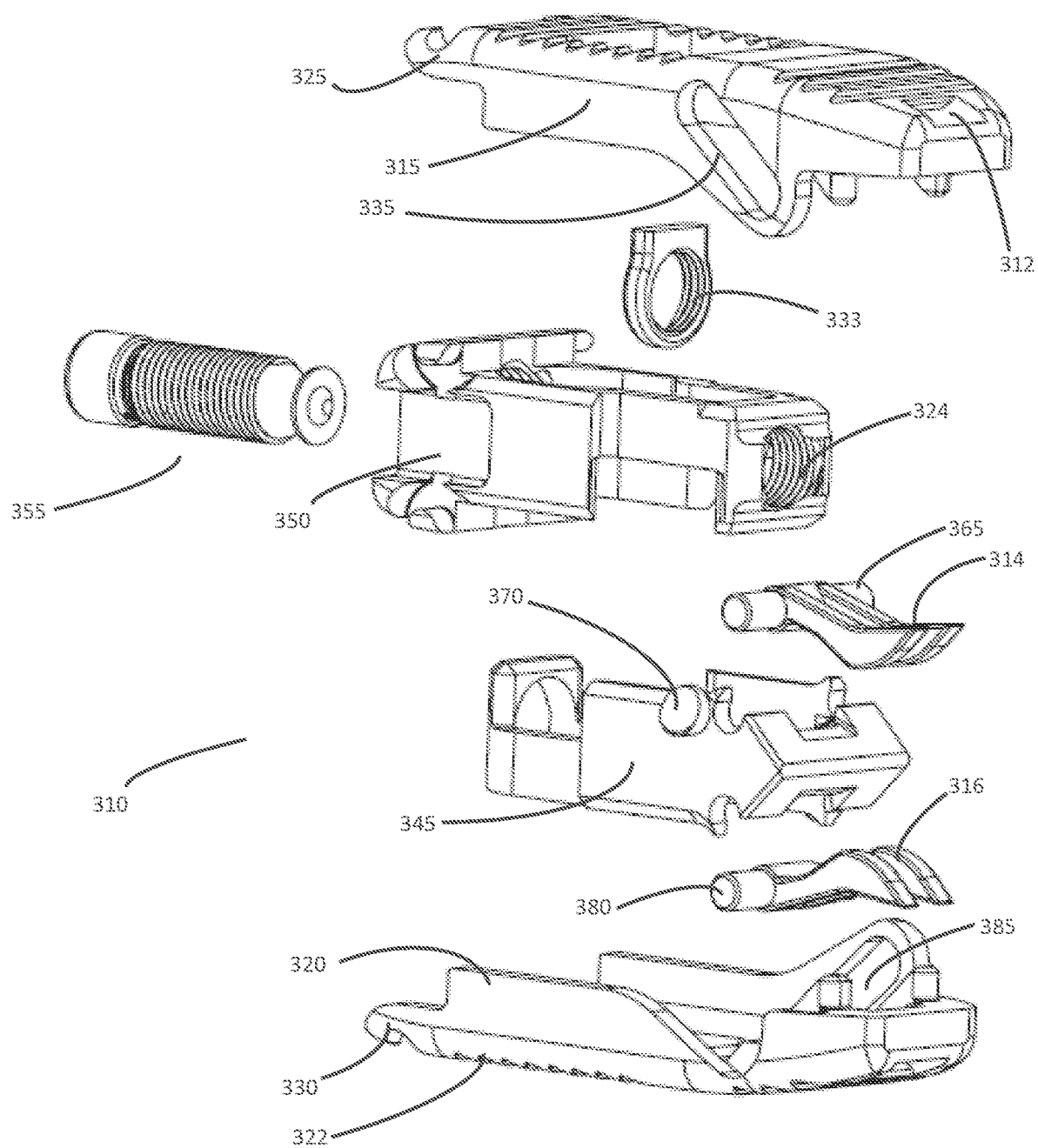
FIG. 12 is an exploded frontal view of another embodiment of an expandable interbody.

FIG. 12 illustrates an alternative embodiment of an expandable interbody 310 that differs from expandable interbody 310 largely in the design of adjustment screw 355 and how it interacts with proximal cage 350 and distal cage 345. Other aspects of expandable interbody 310 largely mirror those of expandable interbody 210: superior shell 315, inferior shell 320, superior hinge point 325, inferior hinge point 330, proximal cage 350, lateral projection 370, angled slot 335, angled slot 385, teeth 322, superior opening 212. Also present in interbody 310 are superior retention prong 314 and inferior retention prong 316. Similar to interbody 210, the point of rotation of superior prong 314 is superior rod 365, and the point of rotation of the inferior prong 316 is inferior rod 380; however, in interbody 310 both superior rod 365 and inferior rod 380 have been configured to engage with the distal end of adjustment screw 355, which in some embodiments includes a flange or groove toward the distal end of adjustment screw 355 to accommodate superior rod 365 and inferior rod 380. This engagement with adjustment screw 355 allows adjustment screw 355 to draw back distal cage 345 so as to collapse or at least partially collapse interbody 310. This configuration can reduce the number of components needed to achieve the desired expansion and contraction of interbody 310.

FIG. 12 also illustrates that the distal end of adjustment screw 355 includes a partially tapered tip. This design, in some embodiments, reduces the amount of friction between the distal end of adjustment screw 355 and distal cage 345.

Also illustrated in FIG. 12 is resistance element 333 that includes a threaded through hole configured to receive adjustment screw 355 and apply a resistance to inadvertent or undesirable rotation of adjustment screw 355. Resistance element 333 is configured to be received by proximal cage 350 and may comprise a material distinct from proximal cage 350. For example, resistance element 333 may comprise a polymer, such as PEEK, in contrast with proximal cage 245, which may comprise a metal, such as titanium or a titanium alloy.

Figure 13:
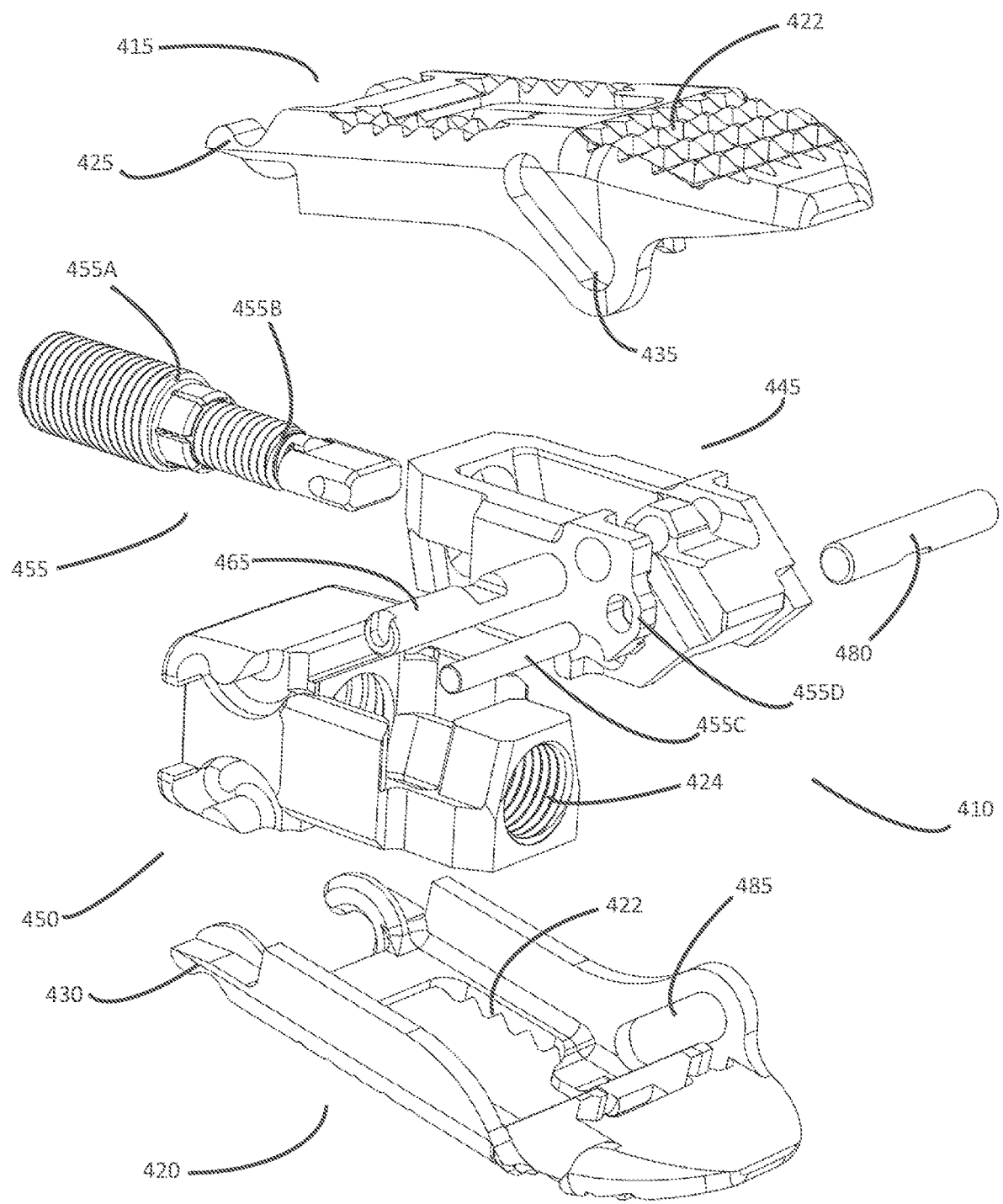
FIG. 13 is an exploded frontal view of another embodiment of an expandable interbody.

FIG. 13 illustrates an alternative embodiment of an expandable interbody 410 that differs from expandable interbody 310 not only because interbody 410 lacks superior and inferior prongs 314, 316 but largely in the design of adjustment screw 455, which in this illustrated embodiment is a twin screw comprising first screw 455A and second screw 455B. First screw 455A contains a threaded bore that threadingly engages the exterior threads of second screw 455B. This design increases the amount of translation or displacement of distal cage 445 relative to proximal cage 450. Rotation of first screw 455A, which is threadingly engaged with threaded bore 424 of proximal cage 450, translates first screw 455A relative to proximal cage 450. This rotation also causes translation of second screw 455, the distal end of which is engaged with and rotational fixed to distal cage 445 by way of cross pin 455C. Cross pin 455C is in turn secured to distal cage 445 by crimping an edge 455D of the hole through which the cross pin is inserted during assembly.

According to some embodiments, the use of a twin screw as in this illustrated embodiment reduces the friction between screw 455 and distal cage 445, such that less torque is required to expand interbody 410. In some embodiments, cross pin 455C is not needed to secure second screw 455B to distal cage 445, which can be achieved simply with a friction fit with the distal end of second screw 455B. However, the use of cross pin 455C may facilitate closure of interbody 410, such as if it needs to be repositioned or removed from the intervertebral space.

Similar to other embodiments disclosed here, interbody 410 includes a superior rod 465 and an inferior rod 480. As in some other embodiments, these rods are positioned and designed to slide in angled slot 435 and angled slot 485, respectively. This illustrated embodiment shows that these rods can be configured to engage the superior shell 415 and inferior shell 420 only by way of their respective angled slots.

As in some other embodiments, superior shell 415 and inferior shell 420 include graft windows as well as protrusions, teeth, or anti-migration features 422. Also, the respective shells at their proximal end include hinge points, which in this embodiments comprise not just a curved aspect but further include a curved wall. Thus, each of superior hinge point 425 and inferior hinge point 430 pivot about the respective proximal engagement features on proximal cage 450, but the additional curved wall may provide additional stability to the overall interbody 410.

EMBODIMENTS

The following embodiments are provided as examples only of specific configurations, materials, arrangements, etc. contemplated by the author of this disclosure:

Embodiment 1. An expandable interbody comprising:
a superior shell having a proximal end and a distal end, the superior shell defining a superior surface extending from the proximal end to the distal end configured to engage an inferior surface of a first vertebral body, the superior shell further comprising a pair of side walls, wherein at least one side wall includes a first angled slot extending distally and away from the superior surface along the side wall;
an inferior shell having a proximal end and a distal end, the inferior shell defining an inferior surface extending from the proximal end to the distal end configured to engage a superior surface of a second vertebral body, the inferior shell further comprising a pair of side walls, wherein at least one side wall includes a second angled slot extending distally and away from the inferior surface along the side wall; and
a control assembly situated between the superior and inferior shells, the control assembly comprising interlocking proximal and distal cages and an adjustment screw defining a longitudinal axis, the proximal cage comprising proximal and distal bores, the distal cage comprising a proximal bore, and the adjustment screw extending through the distal bore of the proximal cage;
wherein a proximal portion of the proximal cage includes a pair of superior hinge points about which the superior shell pivots and a pair of inferior hinge points about which the inferior shell pivots;
wherein the distal cage includes a first lateral projection configured to engage the first angled slot and a second lateral projection configured to engage the second angled slot; and
wherein rotation of the adjustment screw causes the distal cage to translate along the longitudinal axis, which in turn causes the respective distal ends of the superior and inferior shells to move apart from an unexpanded state to an expanded state.

Embodiment 2. The expandable interbody of embodiment 1, wherein the adjustment screw is a twin screw comprising a proximal screw and a distal screw, the proximal screw having a threaded bore open at its distal end with the distal screw threadingly engaged in the threaded bore.

Embodiment 3. The expandable interbody of embodiment 2, wherein a distal end of the distal screw engages the distal cage such that the distal screw is rotationally fixed relative to the distal cage.

Embodiment 4. The expandable interbody of embodiment 1, 2, or 3, wherein the distal bore of the proximal cage is threaded, and wherein the adjustment screw threadingly engages the threaded distal bore of the proximal cage.

Embodiment 5. The expandable interbody of embodiment 1, 2, 3, or 4, wherein a distal end of the adjustment screw is configured to abut an inner surface on the distal end of the distal cage.

Embodiment 6. The expandable interbody of embodiment 1, 2, 3, 4, or 5, wherein the distal cage further comprises a retention pin configured to hold the adjustment screw in place longitudinally relative to the distal cage.

Embodiment 7. The expandable interbody of embodiment 1, 2, 3, 4, 5, or 6, wherein the distal end of the adjustment screw is at least partially tapered.

Embodiment 8. The expandable interbody of embodiment 1, wherein the distal cage further comprises a distal bore that is threaded, and wherein the adjustment screw is threadingly engaged with the threaded distal bore Embodiment 9. The expandable interbody of embodiment 8, wherein the proximal cage further comprises a retention pin configured to hold the adjustment screw in place longitudinally relative to the proximal cage.

Embodiment 10. The expandable interbody of embodiment 1, 2, 3, 4, 5, 6, 7, 8, or 9, wherein the distal cage further comprises distal ramped surfaces configured to slidingly engage respective ramp surfaces on the superior and inferior shells.

Embodiment 11. The expandable interbody of embodiment 1, 2, 3, 4, 5, 6, 7, 8, 9, or 10, wherein the distal cage further comprises a superior rounded surface and an inferior rounded surface each configured to slidingly engage respective interior surfaces of the superior and inferior shells.

Embodiment 12. The expandable interbody of embodiment 11, wherein the superior and inferior rounded surfaces are rods secured to the distal cage.

Embodiment 13. The expandable interbody of embodiment 12, wherein the rods serve as both the first and the second lateral projections of the distal cage.

Embodiment 14. The expandable interbody of embodiment 12 or 13, wherein the rods comprise a material having a lower coefficient of friction than the material comprising the distal cage.

Embodiment 15. The expandable interbody of embodiment 1, 2, 3, 4, 5, 6, 7, 8, 9, 10, 11, 12, 13, or, 14, further comprising deployable superior and/or inferior retention prongs configured to deploy when the expandable interbody is transitioned from the unexpanded state to the expanded state.

Embodiment 16. The expandable interbody of embodiment 15, wherein the superior and/or inferior retention prongs are configured to retract when the expandable interbody is transitioned from the expanded state to the unexpanded state.

Embodiment 17. The expandable interbody of embodiment 15 or 16,
wherein the superior shell comprises a superior opening in the superior surface toward the distal end of the superior shell, the superior opening configured to allow the deployable superior retention prong to pass there through when deployed, and
wherein the inferior shell comprises an inferior opening in the inferior surface toward the distal end of the inferior shell, the inferior opening configured to allow the deployable inferior retention prong to pass there through when deployed.

Embodiment 18. The expandable interbody of embodiment 15, 16, or 17, wherein the superior and/or inferior retention prongs are rotatably connected to the distal cage of the control assembly.

Embodiment 19. The expandable interbody of embodiment 18, wherein translation of the distal cage along the longitudinal axis causes the superior and/or inferior retention prongs to deploy or retract.

Embodiment 20. The expandable interbody of embodiment 15, 16, 17, 18, or 19, as depending from embodiment 12, 13, or 14, wherein the superior and/or inferior retention prongs are attached to the respective rods of the distal cage.

Embodiment 21. The expandable interbody of embodiment 20, wherein the rods of the distal cage are configured to engage the distal end of the adjustment screw that comprises a radial recess for receiving at least a portion of the rods, wherein this engagement longitudinally fixes the distal cage relative to the adjustment screw.

Embodiment 22. The expandable interbody of embodiment 1, 2, 3, 4, 5, 6, 7, 8, 9, 10, 11, 12, 13, 14, 15, 16, 17, 18, 19, 20, or 21, wherein the superior and inferior hinge points comprise respective lateral projections configured to engage proximal portions of the superior and inferior cages, respectively.

Embodiment 23. The expandable interbody of embodiment 1, 2, 3, 4, 5, 6, 7, 8, 9, 10, 11, 12, 13, 14, 15, 16, 17 18, 19, 20, 21, or 22, wherein in the unexpanded state, respective side walls of the superior and inferior shells contact each other so as to enclose the control assembly.

Embodiment 24. The expandable interbody of embodiment 1, 2, 3, 4, 5, 6, 7, 8, 9, 10, 11, 12, 13, 14, 15, 16, 17, 18, 19, 20, 21, 22, or 23, wherein the respective distal ends of the superior and inferior shells are curved so as to enclose the distal end of the distal cage when the interbody is in the unexpanded state.

Embodiment 25. The expandable interbody of embodiment 1, 2, 3, 4, 5, 6, 7, 8, 9, 10, 11, 12, 13, 14, 15, 16, 17, 18, 19, 20, 21, 22, 23, or 24, wherein the superior shell, inferior shell, proximal cage, and distal cage each have at least one opening there through extending from the superior surface of the superior shell to the inferior surface of the inferior shell so as to define a channel for bone growth.

Embodiment 26. The expandable interbody of embodiment 1, 2, 3, 4, 5, 6, 7, 8, 9, 10, 11, 12, 13, 14, 15, 16, 17, 18, 19, 20, 21, 22, 23, 24, or 25, wherein the expandable interbody comprises a titanium alloy.

Embodiment 27. The expandable interbody of embodiment 1, 2, 3, 4, 5, 6, 7, 8, 9, 10, 11, 12, 13, 14, 15, 16, 17, 18, 19 20, 21, 22, 23, 24, 25, or 26, wherein the interbody further comprises a resistance element configured to resist rotation of the adjustment screw.

Embodiment 28. The expandable interbody of embodiment 27, wherein the resistance element comprises a polymer.

Embodiment 29. The expandable interbody of embodiment 1, 2, 3, 4, 5, 6, 7, 8, 9, 10, 11, 12, 13, 14, 15, 16, 17, 18, 19 20, 21, 22, 23, 24, 25, 26, 27, or 28, wherein at least one of the superior shell, inferior shell, proximal cage, distal cage, and adjustment screw comprises a porous material.

Embodiment 30. The expandable interbody of embodiment 29, wherein the porous material comprises two or more layers of porous sheets that have been bonded together to form a uniform material.

Embodiment 31. The expandable interbody of embodiment 1, 2, 3, 4, 5, 6, 7, 8, 9, 10, 11, 12, 13, 14, 15, 16, 17, 18, 19 20, 21, 22, 23, 24, 25, 26, 27, 28, 29, or 30, wherein the superior and inferior shells are configured to at least partially nest within each other when the interbody is in the unexpanded state.

Embodiment 32. The expandable interbody of embodiment 1, 2, 3, 4, 5, 6, 7, 8, 9, 10, 11, 12, 13, 14, 15, 16, 17, 18, 19 20, 21, 22, 23, 24, 25, 26, 27, 28, 29, 30, or 31, wherein the proximal and distal cages further comprise side walls configured to contact respective inside surfaces of the side walls of the superior and inferior shells to provide structural support to the interbody.

Embodiment 33. The expandable interbody of embodiment 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, or 32, wherein an edge of at least one side wall of the superior shell comprises one or more projections and an edge of at least one side wall of the inferior shell comprises one or more depressions configured to receive the one or more projections of the superior shell so as to provide the interbody with greater structural integrity when the interbody is in the unexpanded state.

Embodiment 34. The expandable interbody of embodiment 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, or 33, wherein the superior surface of the superior shell and/or the inferior surface of the inferior shell further comprises a layer of a porous material positioned within a cutout or depression in the superior and/or inferior surfaces.

Embodiment 35. The expandable interbody of embodiment 34, wherein the layer of porous material comprises one or more sheets of porous titanium alloy.

Embodiment 36. An inserter for use with the expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, or 35, the inserter comprising:
- a handle portion that includes an extension portion with a cannula extending from a proximal end of the handle to a distal end of the extension portion;
- an engagement portion located on a distal end of the extension portion, the engagement portion including an engagement mechanism configured to engage the interbody, and at least one counter torque extension configured to prevent the interbody from rotating while the engagement mechanism engages with or disengages from the interbody; and
- an expansion tool comprising a handle and an extension configured to slide through and rotate within the cannula of the handle portion, the extension comprising a tip configured extend into the interbody so as to engage with the adjustment screw;
- wherein rotation of the expansion tool when engaged with the adjustment screw causes the interbody to transition from the unexpanded state to the expanded state or from the expanded state to the unexpanded state.

Embodiment 37. The inserter of embodiment 36, wherein the handle further comprises an engagement knob configured to rotate the engagement mechanism.

Embodiment 38. The inserter of embodiment 36 or 37, wherein the handle further comprises an expansion indicator configured to indicate the degree of expansion of the interbody achieved by rotating the expansion tool.

Embodiment 39. The inserter of embodiment 38, wherein the expansion tool is configured to provide an initial degree of expansion of the interbody.

Embodiment 40. The inserter of embodiment 39, wherein the initial degree of expansion is greater than about 0°, greater than about 2°, greater than about 4°, or greater than about 6°.

Embodiment 41. A method of implanting the expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, the method comprising:
- with an inserter, positioning the interbody in a collapsed state in an intervertebral disc space;
- expanding the interbody by rotating a control knob on the inserter that in turn rotates the adjustment screw; and
- releasing the expanded interbody from the inserter.

Embodiment 42. The method of embodiment 41, further comprising, before releasing the expanded interbody from the inserter, injecting a material that promotes bone growth into the interbody through an opening in the proximal end of the interbody.

Embodiment 43. A method of implanting the expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, the method comprising:
- with the inserter of embodiment 36, 37, 38, 39, or 40, positioning the interbody in a collapsed state in an intervertebral disc space;
- expanding the interbody by rotating a control knob on the inserter that in turn rotates the adjustment screw; and
- releasing the expanded interbody from the inserter.

Embodiment 44. The method of embodiment 42, further comprising, before releasing the expanded interbody from the inserter, injecting a material that promotes bone growth into the interbody through a proximal opening in the cannula.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It should be noted that the instrument, system, and method described herein is illustrated in a posterior approach, but that the instrument, system, and method described herein may be used in other surgical procedures to include a lateral or an anterior approach.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventor for carrying out the embodiments of the present disclosure. Of course, variations on these described embodiments will become apparent to those of ordinary skill in the art upon reading the foregoing description. The inventor expects skilled artisans to employ such variations as appropriate, and the inventor intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:

1. An expandable interbody comprising:
a superior shell having a proximal end and a distal end, the superior shell defining a superior surface extending from the proximal end to the distal end, the superior shell further comprising at least one side wall, wherein the at least one side wall includes a first slot extending distally and away from the superior surface along the side wall;
an inferior shell having a proximal end and a distal end, the inferior shell defining an inferior surface extending from the proximal end to the distal end configured to engage a superior surface of a second vertebral body, the inferior shell further comprising at least one side wall, wherein the at least one side wall includes a second slot extending distally and away from the inferior surface along the side wall; and
a control assembly situated between the superior and inferior shells, the control assembly comprising directly interlocking proximal and distal cages and an adjustment screw defining a longitudinal axis, the proximal cage comprising proximal and distal bores, the distal cage comprising a proximal bore, and the adjustment screw extending through the distal bore of the proximal cage;
wherein the proximal ends of the superior and inferior shells are configured to pivotally engage respective portions of the proximal cage;
wherein the distal cage includes a first lateral projection configured to engage the first slot and a second lateral projection configured to engage the second slot; and
wherein rotation of the adjustment screw causes the distal cage to translate along the longitudinal axis, which in turn causes the respective distal ends of the superior and inferior shells to move apart from an unexpanded state to an expanded state.

2. The expandable interbody of claim 1, wherein the adjustment screw is a twin screw comprising a proximal screw and a distal screw, the proximal screw having a threaded bore open at its distal end with the distal screw threadingly engaged in the threaded bore.

3. The expandable interbody of claim 2, wherein a distal end of the distal screw engages the distal cage such that the distal screw is rotationally fixed relative to the distal cage.

4. The expandable interbody of claim 1, wherein the distal bore of the proximal cage is threaded, and wherein the adjustment screw threadingly engages the threaded distal bore of the proximal cage.

5. The expandable interbody of claim 1, wherein the distal cage further comprises a retention pin configured to hold the adjustment screw in place relative to the distal cage.

6. The expandable interbody of claim 1, wherein the distal cage further comprises distal ramped surfaces configured to slidingly engage respective ramp surfaces on the superior and inferior shells.

7. The expandable interbody of claim 1, wherein the distal cage further comprises a superior rounded surface and an inferior rounded surface each configured to slidingly engage respective interior surfaces of the superior and inferior shells.

8. The expandable interbody of claim 1, wherein the respective distal ends of the superior and inferior shells are curved so as to enclose the distal end of the distal cage when the interbody is in the unexpanded state.

9. The expandable interbody of claim 1, wherein each of the lateral extensions defines an axis and each lateral extension terminates with a surface that is not perpendicular to its respective axis.

10. The expandable interbody of claim 1, wherein the pivotal engagement between the proximal cage and the superior and inferior shells, respectively, is achieved with a pair of superior extensions on the proximal cage configured to engage a portion of the superior shell and a pair of inferior extensions on the proximal cage configured to engage a portion of the inferior shell.

11. The expandable interbody of claim 10, wherein each of the respective portions of the superior and inferior shells comprises a pair of curved projections that extend proximally from the superior and inferior shells.

12. The expandable interbody of claim 11, wherein each of the curved projections is configured to engage with curved cutouts on the proximal cage.

13. The expandable interbody of claim 11, wherein each of the curved projections is configured to engage with the superior and inferior extensions of the proximal cage.

14. The expandable interbody of claim 1, wherein the proximal bore of the proximal cage is threaded.

15. An interbody system comprising:
an expandable interbody comprising:
a superior shell having a proximal end and a distal end, the superior shell defining a superior surface extending from the proximal end to the distal end, the superior shell further comprising at least one side wall, wherein the at least one side wall includes a first slot extending distally and away from the superior surface along the side wall;
an inferior shell having a proximal end and a distal end, the inferior shell defining an inferior surface extending from the proximal end to the distal end configured to engage a superior surface of a second vertebral body, the inferior shell further comprising at least one side wall, wherein the at least one side wall includes a second slot extending distally and away from the inferior surface along the side wall; and a control assembly situated between the superior and inferior shells, the control assembly comprising interlocking proximal and distal cages and an adjustment screw defining a longitudinal axis, the proximal cage comprising proximal and distal bores, the distal cage comprising a proximal bore, and the adjustment screw extending through the distal bore of the proximal cage;

wherein the proximal ends of the superior and inferior shells are configured to pivotally engage respective portions of the proximal cage;

wherein the distal cage includes a first lateral projection configured to engage the first slot and a second lateral projection configured to engage the second slot; and wherein rotation of the adjustment screw causes the distal cage to translate along the longitudinal axis, which in turn causes the respective distal ends of the superior and inferior shells to move apart from an unexpanded state to an expanded state; and an inserter configured to engage the expandable interbody, the inserter comprising:

a handle portion that includes an extension portion with a cannula extending from a proximal end of the handle to a distal end of the extension portion;

an engagement portion located on a distal end of the extension portion, the engagement portion including an engagement mechanism configured to engage the expandable interbody, and at least one counter torque extension configured to prevent the interbody from rotating while the engagement mechanism engages with or disengages from the interbody; and an expansion tool comprising a handle and an extension configured to slide through and rotate within the cannula of the handle portion, the extension comprising a tip configured extend into the expandable interbody so as to engage with the adjustment screw;

wherein rotation of the expansion tool when engaged with the adjustment screw causes the expandable interbody to transition from the unexpanded state to the expanded state or from the expanded state to the unexpanded state.

16. The interbody system of claim 15, wherein the handle further comprises an engagement knob configured to rotate the engagement mechanism.

17. The interbody system of claim 15, wherein the handle further comprises an expansion indicator configured to indicate the degree of expansion of the expandable interbody achieved by rotating the expansion tool.

18. The interbody system of claim 17, wherein the expansion tool is configured to provide an initial degree of expansion of the expandable interbody.

19. The interbody system of claim 18, wherein the initial degree of expansion is greater than about 0°, greater than about 2°, greater than about 4°, or greater than about 6°.

20. The interbody system of claim 15, wherein the proximal bore of the proximal cage is threaded, and wherein the engagement mechanism comprises a threaded element configured to threadingly engage the threaded proximal bore.

* * * * *